(12) United States Patent
Kato

(10) Patent No.: US 11,559,512 B2
(45) Date of Patent: Jan. 24, 2023

(54) COMPOSITION FOR PREVENTION, ALLEVIATION, AND/OR TREATMENT OF HEAT ILLNESS

(71) Applicant: TOYO UNIVERSITY, Tokyo (JP)

(72) Inventor: Kazunori Kato, Kawagoe (JP)

(73) Assignee: TOYO UNIVERSITY, Tokyo (JP)

( * ) Notice: Subject to any disclaimer, the term of this patent is extended or adjusted under 35 U.S.C. 154(b) by 336 days.

(21) Appl. No.: 16/650,615

(22) PCT Filed: Sep. 26, 2018

(86) PCT No.: PCT/JP2018/035650
§ 371 (c)(1),
(2) Date: May 28, 2020

(87) PCT Pub. No.: WO2019/065718
PCT Pub. Date: Apr. 4, 2019

(65) Prior Publication Data
US 2020/0297694 A1    Sep. 24, 2020

(30) Foreign Application Priority Data
Sep. 26, 2017  (JP) .............................. JP2017-184343

(51) Int. Cl.
| | |
|---|---|
| *A61K 36/752* | (2006.01) |
| *A61K 31/366* | (2006.01) |
| *A23K 20/126* | (2016.01) |
| *A23K 20/158* | (2016.01) |
| *A23L 33/12* | (2016.01) |
| *A23L 33/105* | (2016.01) |
| *A61K 31/20* | (2006.01) |
| *A61K 31/353* | (2006.01) |

(52) U.S. Cl.
CPC .......... *A61K 31/366* (2013.01); *A23K 20/126* (2016.05); *A23K 20/158* (2016.05); *A23L 33/105* (2016.08); *A23L 33/12* (2016.08); *A61K 31/20* (2013.01); *A61K 31/353* (2013.01); *A61K 36/752* (2013.01)

(58) Field of Classification Search
None
See application file for complete search history.

(56) References Cited

U.S. PATENT DOCUMENTS

| | | | |
|---|---|---|---|
| 2017/0000746 A1 | 1/2017 | Preuss | |
| 2017/0196242 A1 | 7/2017 | Koike et al. | |
| 2019/0083382 A1* | 3/2019 | Burke | ............. A61K 8/9794 |

FOREIGN PATENT DOCUMENTS

| | | | |
|---|---|---|---|
| JP | 2007-001937 A | | 1/2007 |
| JP | 2015-140347 A | | 8/2015 |
| JP | 2016/007149 | * | 1/2016 |
| JP | 2016-007149 A | | 1/2016 |
| JP | 2016-037498 A | | 3/2016 |
| WO | WO 2015/127320 A2 | | 8/2015 |

OTHER PUBLICATIONS

Ako Kasei Co., Ltd., Release of "coconut oil salty candy" helpful in coping with heat-stroke, My life news, obtained from the Internet at URL: <http://mylifenews.net/drink/2015/05/post-1927.html>, pp. 1-3, non-official translation, dated Dec. 3, 2018, as obtained from the Internet on May 26, 2015, 4 pages.

Shu, Z., et al., "Tangeretin exerts anti-neuroinflammatory effects via NF-κB modulation in lipopolysaccharide-stimulated microglial cells," *International Immunopharmacology*, 19:275-282 (2014).

Extended European search report including the supplementary European search report and the European search opinion, received in European Application No. 18862232.8 dated May 14, 2021.

* cited by examiner

*Primary Examiner* — Ralph J Gitomer
(74) *Attorney, Agent, or Firm* — Crowell & Moring LLP

(57) ABSTRACT

This application provides a composition for preventing, alleviating and/or treating a heat illness, or cytotoxicity of cells such as vascular endothelial cells caused by load of heat stress and/or aberration associated with the production and release of a fever-inducing inflammatory cytokine(s) from blood cells caused by load of heat stress in a subject, comprising at least one substance selected from the group consisting of auraptene, tangeretin, and medium chain fatty acid as an active ingredient.

20 Claims, 19 Drawing Sheets

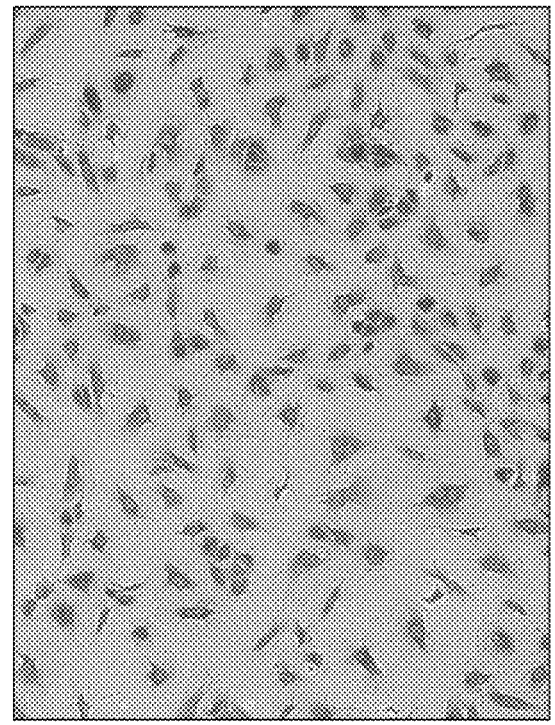
Fig. 1A 37°C
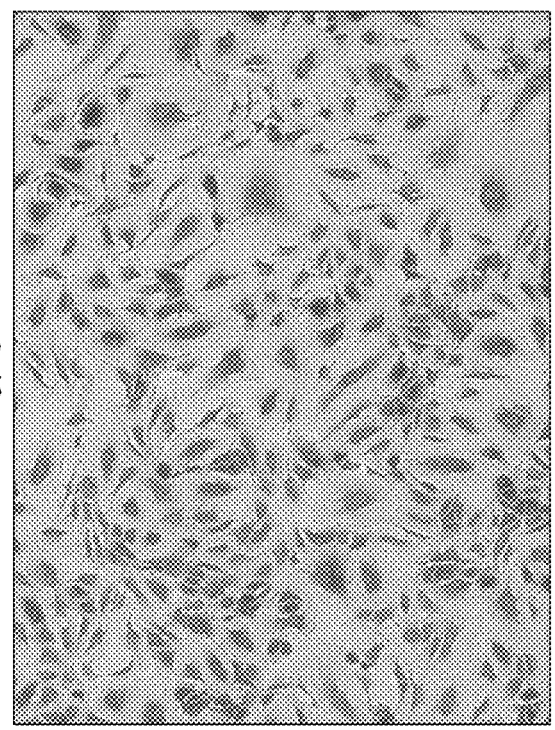
Fig. 1B 40°C

37°C

40°C

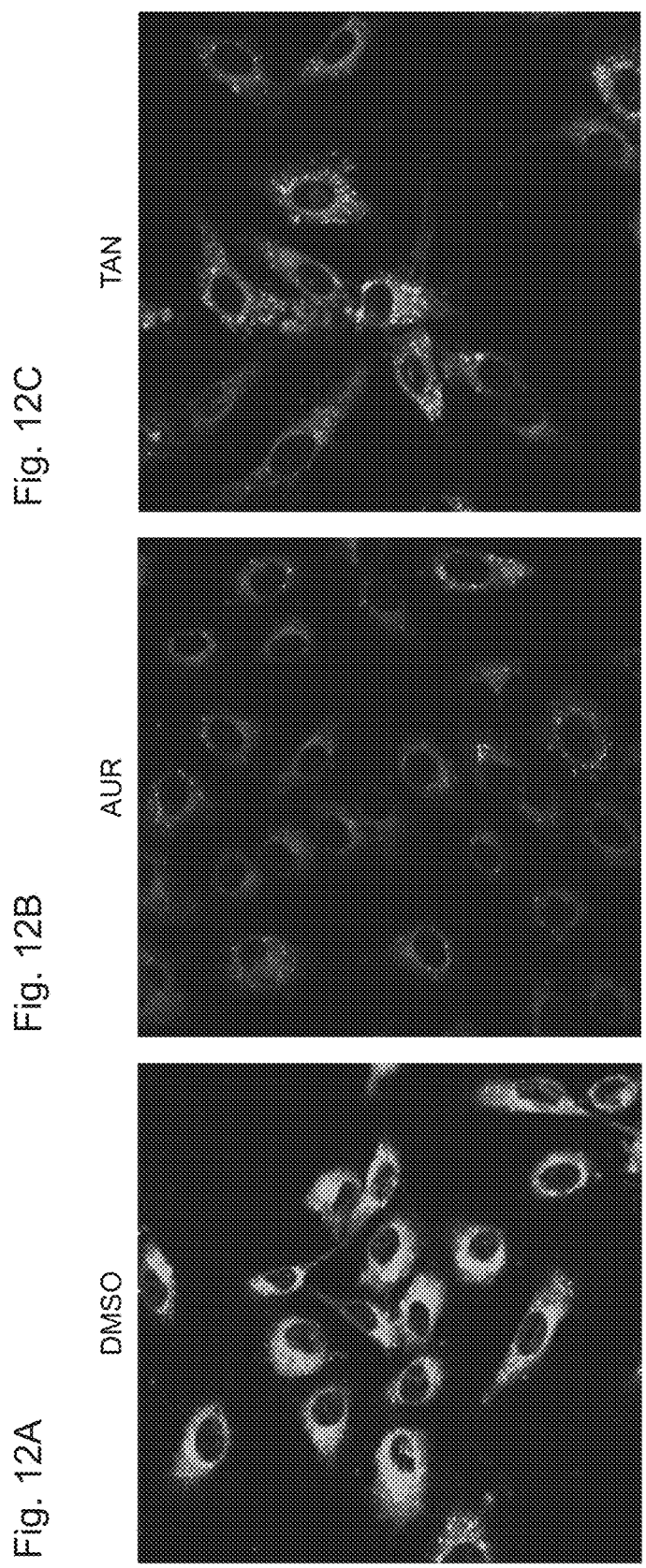

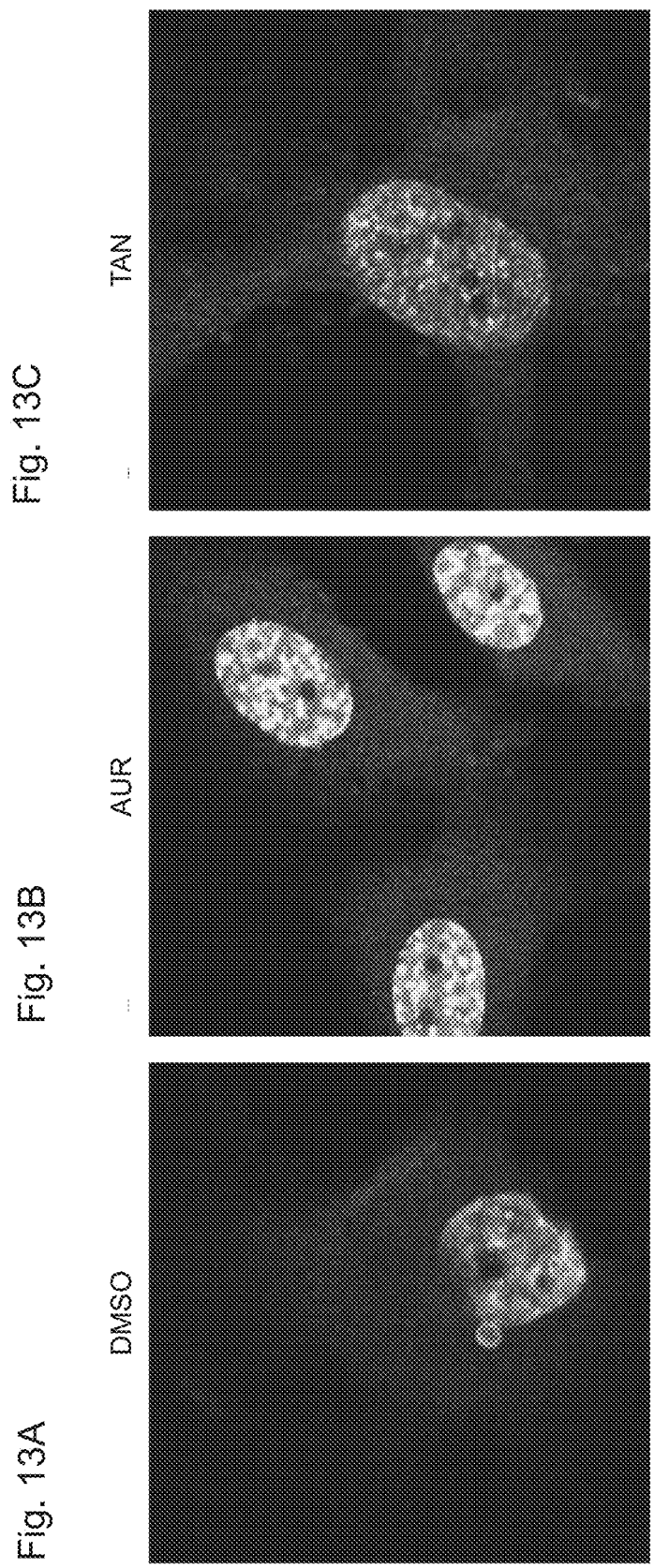

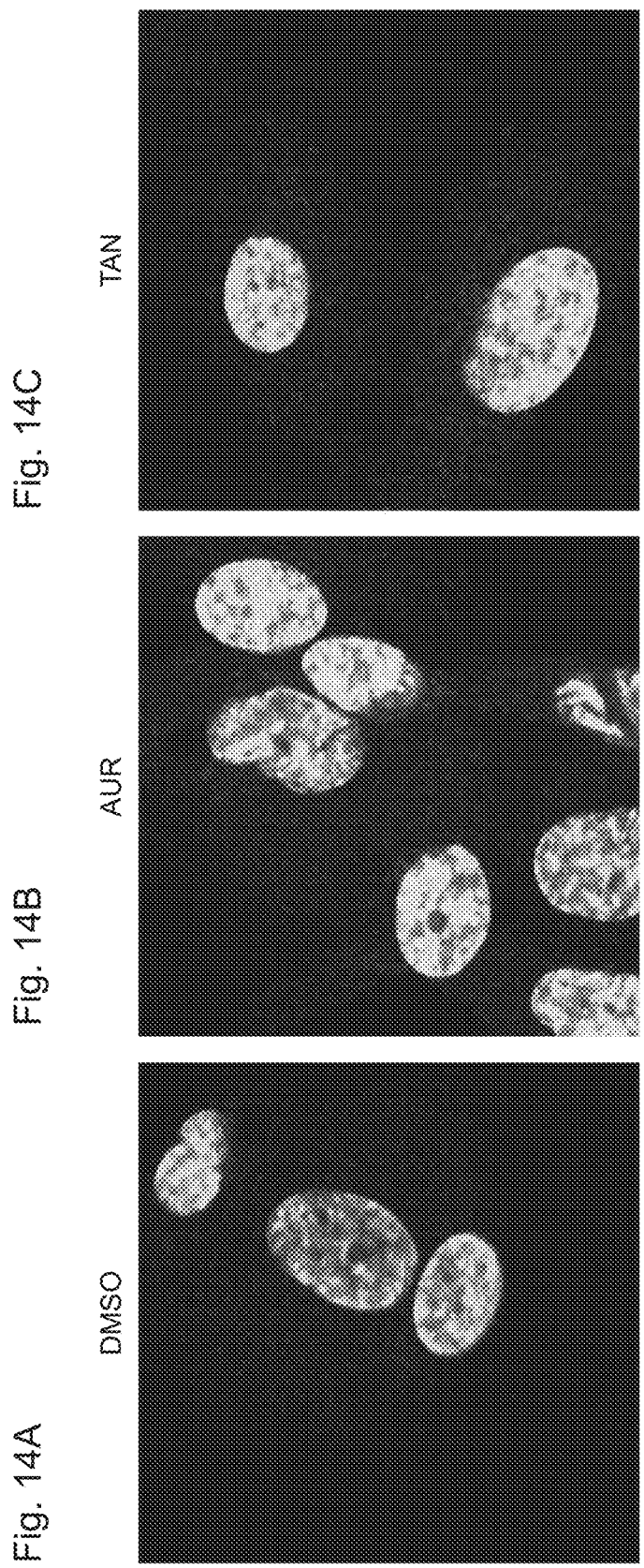

Fig. 15A
Fig. 15B
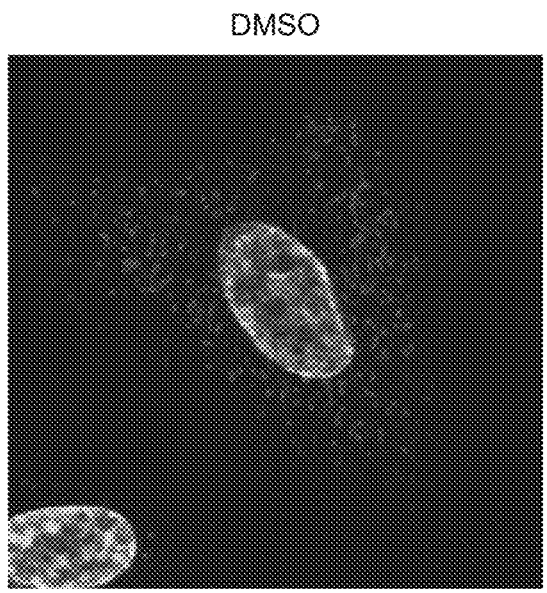
DMSO
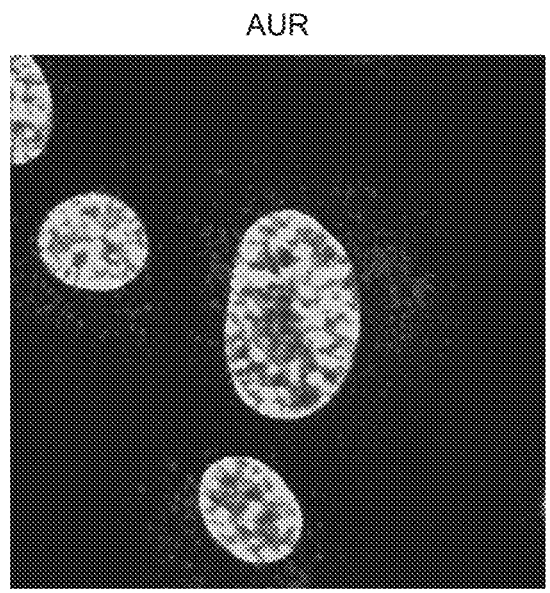
AUR

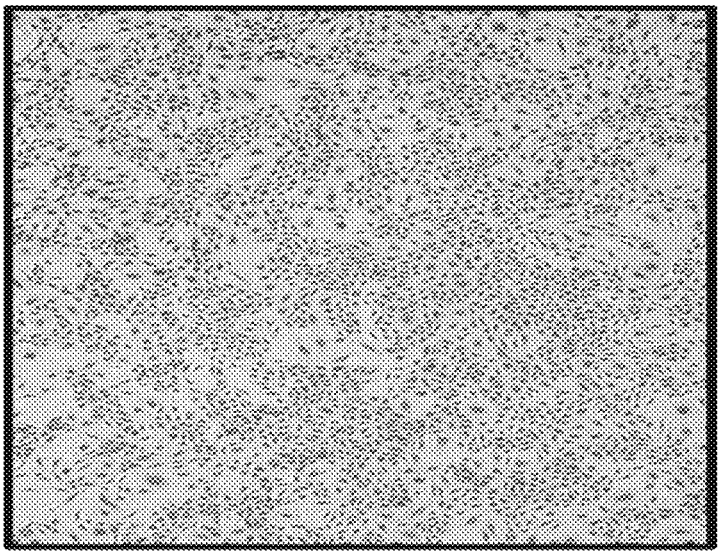
Fig. 19A Auraptene (5 μM)
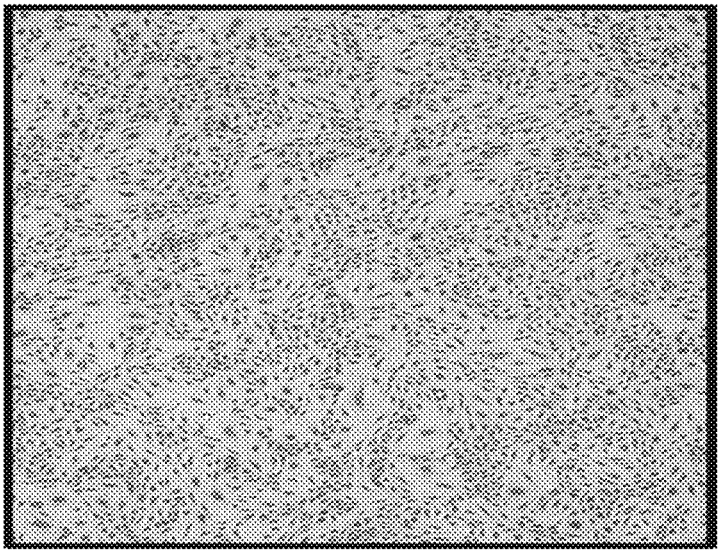
Fig. 19B Auraptene (5 μM) + medium chain fatty acid (64 μM/ml)
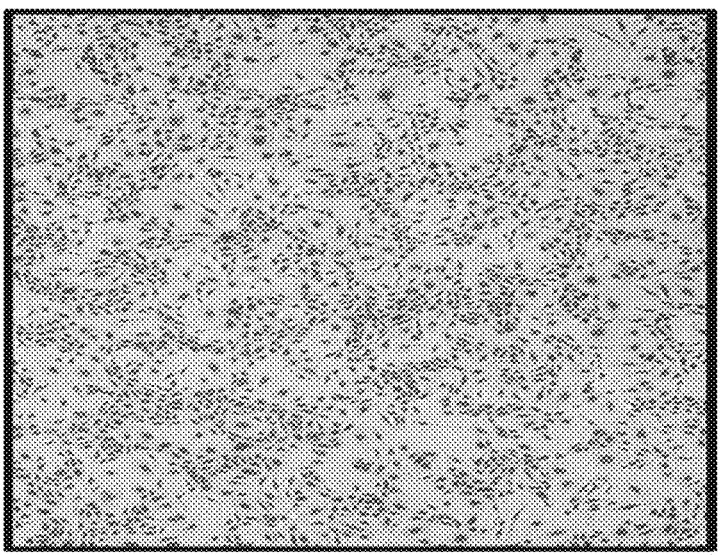
Fig. 19C Auraptene (5 μM) + medium chain fatty acid (8 μM/ml)

COMPOSITION FOR PREVENTION, ALLEVIATION, AND/OR TREATMENT OF HEAT ILLNESS

RELATED APPLICATIONS

This application is a 371 application of PCT/JP2018/035650 having an international filing date of Sep. 26, 2018, which claims priority to JP 2017-184343 filed Sep. 26, 2017, the entire content of each of which is incorporated herein by reference.

TECHNICAL FIELD

The present invention relates to a composition capable of preventing, alleviating and/or treating a heat illness, or cytotoxicity of cells such as vascular endothelial cells caused by load of heat stress and/or aberration associated with the production and release of a fever-inducing inflammatory cytokine(s) from blood cells caused by load of heat stress, comprising at least one substance selected from the group consisting of auraptene, tangeretin, and medium chain fatty acid.

BACKGROUND ART

The heat illness refers to a condition in which heat in the body can no longer be released because the body temperature or body fluid regulatory function of the body is damaged by sunlight, air temperature, etc. The heat illness is divided into three stages from mild to severe cases and causes dizziness, syncope, and heat cramp caused by muscle stiffness or the like, as mild cases. Moderate symptoms such as headache, vomiting, and diarrhea occur with an overlap and are regarded as conventional heat exhaustion. Severe symptoms such as disturbance of consciousness, hyperventilation, and disturbance of motility occur with an overlap with moderate symptoms and are regarded as conventional heatstroke. Although possible causes of the heat illness are environmental or physical factors, severe heat illness reportedly becomes prone to recurrence. However, the number of patients with heat illness is increasing because of climate change caused by global warming, etc., and partly because of the absence of effective prophylactic or therapeutic drugs for heat illness. Thus, the heat illness is considered a serious social problem. There are urgent patients with heat illness not only in summer but throughout the year, and elderly people and infants are especially at higher risk.

The influence of heat stress is proposed as one of the causes of the heat illness. The heat stress refers to stress that causes various dysfunctions in living bodies due to elevation of body temperature. It is considered that in vivo heat stress disrupts homeostasis such as body temperature regulation, body fluid balance, or blood circulation adjustment and consequently damages blood vessels so that vascular endothelial cells undergo heat stress, leading to intracellular disturbance of metabolism. This reportedly causes tissues or cells to fall into a lack of oxygen and poor nutrition, causing a critical heat illness due to dysfunction. Hence, measures such as development of novel prophylactic or therapeutic drugs or symptomatic therapy have been longed for, in addition to hydration or supplementation with salts (sodium, magnesium, etc.) and sugars, which is a conventional method for preventing a heat illness.

As for previously reported prophylactic or therapeutic agents for heat illness, there are disclosed, for example, a prophylactic agent for heat illness containing a fat or oil composition comprising α-linolenic acid (Patent Literature 1), an agent alleviating heat stress in livestock, containing trehalose as an active ingredient (Patent Literature 2), a composition for alleviating heat stress, containing at least sake cake and malted rice (Patent Literature 3), and a method for preventing or treating a heat stress symptom using astaxanthin and a lactic casein hydrolysate in combination (Patent Literature 4).

CITATION LIST

Patent Literature

Patent Literature 1: JP Patent Publication (Kokai) No. 2016-37498 A (2016)
Patent Literature 2: JP Patent Publication (Kokai) No. 2015-140347 A (2015)
Patent Literature 3: JP Patent Publication (Kokai) No. 2007-001937 A (2007)
Patent Literature 4: US 2017/0000746 A1

SUMMARY OF INVENTION

Technical Problem

As described above, there has been a demand for novel prophylactic or therapeutic drugs, symptomatic therapy, etc., because a possible cause of the onset of a heat illness (or heatstroke) is tissue or cell dysfunction associated with a lack of oxygen and/or poor nutrition in tissues or cells resulting from damage on blood vessels exposed to heat stress.

Accordingly, an object of the present invention is to provide a novel method for preventing and/or treating a heat illness, comprising preventing, alleviating and/or treating the cytotoxicity, such as disturbance of metabolism or dysfunction, of cells such as vascular endothelial cells due to heat stress.

Solution to Problem

The present inventors have conducted diligent studies to attain the object and consequently have now found that the cytotoxicity, such as disturbance of metabolism, dysfunction, or cell death, of cells such as vascular endothelial cells caused by heat stress, and the production and release of a fever-inducing inflammatory cytokine(s) from blood cells caused by the load of heat stress can be reduced by adding at least one substance selected from the group consisting of auraptene, tangeretin, and medium chain fatty acid to cultured vascular endothelial cells or cultured blood cells (e.g., lymphocytes and leukocytes) placed under heat stress conditions. The at least one substance selected from the group consisting of auraptene, tangeretin and medium chain fatty acid has now been found to be able to prevent, alleviate and/or treat a heat illness by suppressing the cytotoxicity described above due to heat stress, and/or decreasing the production and release of a fever-inducing inflammatory cytokine(s) from blood cells caused by the load of heat stress. On the basis of these findings, the present invention has been completed.

Specifically, the present invention includes the following features.

[1] A composition for preventing, alleviating and/or treating a heat illness in a subject, comprising at least one substance selected from the group consisting of auraptene, tangeretin and medium chain fatty acid as an active ingredient.

[2] The composition according to [1], wherein the heat illness comprises cytotoxicity of vascular endothelial cells caused by load of heat stress.

[3] The composition according to [1] or [2], wherein the heat illness comprises aberration associated with the production and release of a fever-inducing inflammatory cytokine(s) from blood cells caused by load of heat stress.

[4] The composition according to any of [1] to [3], wherein the composition has at least one effect selected from the group consisting of an effect of suppressing the cytotoxicity of vascular endothelial cells caused by the load of heat stress, an effect of increasing lipid metabolism, and an effect of decreasing the production and release of a fever-inducing inflammatory cytokine(s) from blood cells caused by load of heat stress.

[5] The composition according to any of [1] to [4], wherein the subject is a homeothermic animal.

[6] The composition according to [5], wherein the homeothermic animal is a human, a livestock animal, or a pet animal.

[7] The composition according to any of [1] to [6], wherein the auraptene and/or the tangeretin is a synthetic substance or is from an extract of a plant material of a citrus.

[8] The composition according to [7], wherein the plant material is a fruit.

[9] The composition according to [7] or [8], wherein the auraptene is a synthetic substance or is from a fruit extract of at least one citrus selected from *Citrus natsudaidai*, *Citrus hassaku*, *Citrus* x *paradisi*, *Citrus junos*, *Citrus sphaerocarpa*, and *Citrus grandis*.

[10] The composition according to [7] or [8], wherein the tangeretin is a synthetic substance or is from a fruit extract of at least one citrus selected from *Citrus reticulata* and *Citrus depressa*.

[11] The composition according to any of [1] to [8], wherein the medium chain fatty acid is medium chain triglyceride (MCT).

[12] The composition according to any of [1] to [11], wherein the composition is a food or drink, or a medicament.

[13] The composition according to any of [1] to [11], wherein the composition is animal feed or a feed additive.

[14] A method for preventing, alleviating and/or treating a heat illness, or cytotoxicity of vascular endothelial cells caused by load of heat stress and/or aberration associated with the production and release of a fever-inducing inflammatory cytokine(s) from blood cells caused by load of heat stress in a subject, comprising administering or providing a composition according to any of [1] to [13] to the subject.

The present specification encompasses the contents disclosed in Japanese Patent Application No. 2017-184343 from which the present application claims the priority.

Effects of Invention

According to the present invention, at least one substance selected from the group consisting of auraptene, tangeretin and medium chain fatty acid, administered or provided to a subject, can suppress the cytotoxicity of cells such as vascular endothelial cells caused by load of heat stress and/or can decrease the production and release of a fever-inducing inflammatory cytokine(s) from blood cells caused by load of heat stress, and therefore achieves a novel type of measures against the heat illness.

BRIEF DESCRIPTION OF DRAWINGS

FIGS. 1A and 1B show morphological change of human umbilical vein vascular endothelial cells (hereinafter, also simply referred to as "human vascular endothelial cells" or "HUVECs") caused by the load of heat stress. When the human vascular endothelial cells (HUVECs) were cultured at 37° C. (FIG. 1A) or 40° C. (FIG. 1B), morphological change (i.e., cellular shrinkage) was found 1 day later at 40° C., and cell proliferation inhibition and further, cell death were observed 2 days later. The cells were stained with crystal violet and photographed under a phase contrast microscope.

FIGS. 12A, 12B and 12C show confocal laser scanning micrographs of human vascular endothelial cells (HUVECs) showing that the addition of auraptene (AUR) or tangeretin (TAN) decreased the amount of fat droplets accumulated in the HUVECs, i.e., enhanced intracellular fatty acid metabolism, when the cells were cultured under heat stress load at 40° C. for 2 days (FIGS. 12B and 12C, respectively). A micrograph taken when DMSO was added instead of the component is shown for a control (FIG. 12A). BODIPY488 was used for staining the fat droplets.

FIGS. 13A, 13B and 13C show confocal laser scanning micrographs of human vascular endothelial cells (HUVECs) showing increase in the expression of PPARα by auraptene (AUR) or tangeretin (TAN) when the cells were cultured at 40° C. for 1 day (FIGS. 13B and 13C, respectively). A micrograph taken when DMSO was added instead of the component is shown for a control (FIG. 13A). The expression of PPARα was detected by anti-PPARα antibody staining.

FIGS. 14A, 14B and 14C show a confocal laser scanning micrograph of human vascular endothelial cells (HUVECs) showing increase in the expression of PPARγ by auraptene (AUR) when the cells were cultured at 40° C. for 1 day (FIG. 14B). A micrograph taken when DMSO was added instead of the component is shown for a control (FIG. 14A). However, increase in the expression of PPARγ by tangeretin (TAN) was not observed (FIG. 14C). In this context, the expression of PPARγ was detected by anti-PPARγ antibody staining.

FIGS. 15A and 15B show a confocal laser scanning micrograph of human vascular endothelial cells (HUVECs) showing that change in ABCD3 expression by the addition of auraptene (AUR) was not found when the cells were cultured at 40° C. for 3 days (FIG. 15B). A micrograph taken when DMSO was added instead of the component is shown for a control (FIG. 15A). In this context, the expression of ABCD3 was detected by Alexa 647-anti-ABCD3 antibody staining.

FIGS. 19A, 19B and 19C show phase contrast micrographs showing the effect of suppressing heat stress-induced cell death by combined use of auraptene and medium chain fatty acid when human vascular endothelial cells (HUVECs) underwent the load of heat stress. FIG. 19A shows results about auraptene (5 µM) used alone, FIG. 19B shows results about the combined use of auraptene (5 µM) and medium chain fatty acid (64 µl/ml), and FIG. 19C shows results about the combined use of auraptene (5 µM) and medium chain fatty acids (8 µl/ml). In the figure, the medium chain fatty acid used was MCT (medium chain triglyceride) oil (The Nisshin OilliO Group, Ltd., Japan) which is composed mainly of C8 to C12 medium chain fatty acid.

DESCRIPTION OF EMBODIMENTS

Figure 2:
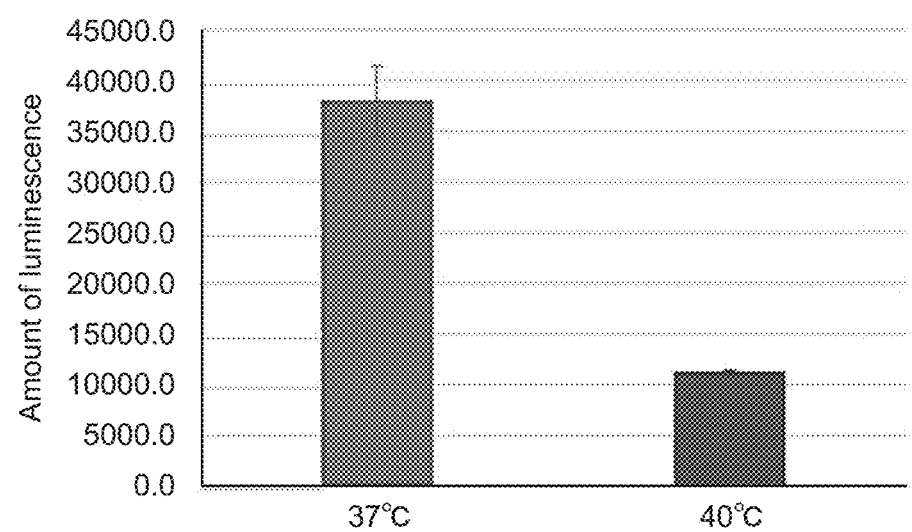
FIG. 2 shows decrease in the amount of ATP in human vascular endothelial cells (HUVECs) caused by the load of heat stress (culture at 40° C. for 3 days). Results of measuring the amount of ATP in HUVECs after culture at 37° C. for 3 days are shown as a comparative control. In this context, the amount of ATP in the cells was measured by use of the luciferase luminescence method.

According to the first aspect, the present invention provides a composition for preventing, alleviating and/or treating a heat illness in a subject, comprising at least one substance selected from the group consisting of auraptene, tangeretin and medium chain fatty acid as an active ingredient.

According to an embodiment of the present invention, the heat illness comprises cytotoxicity (e.g., disturbance of metabolism, dysfunction, and cell death) of cells such as vascular endothelial cells caused by load of heat stress, and/or aberration (e.g., fever and high body temperature) associated with the production and release of a fever-inducing inflammatory cytokine(s) from blood cells caused by load of heat stress. Hence, the composition comprising at least one substance selected from the group consisting of auraptene, tangeretin and medium chain fatty acid as an active ingredient, administered or provided to a subject, can prevent, alleviate and/or treat cytotoxicity of cells such as vascular endothelial cells caused by load of heat stress and/or aberration (e.g., fever and high body temperature) associated with the production and release of a fever-inducing inflammatory cytokine(s) from blood cells caused by load of heat stress.

Thus, according to the second aspect, the present invention provides a method for preventing, alleviating and/or treating a heat illness, or cytotoxicity of cells such as vascular endothelial cells caused by load of heat stress and/or aberration (e.g., fever and high body temperature) associated with the production and release of a fever-inducing inflammatory cytokine(s) from blood cells caused by load of heat stress in a subject, comprising administering or providing the composition to the subject.

As used herein, the "fever-inducing inflammatory cytokine(s)" refers to an inflammatory cytokine(s) that induces fever, as used interchangeably with a pyrogenic factor. Examples thereof include interleukin 6 (IL-6) and C-C motif chemokine ligand 2 (CCL-2). It is known that the level of IL-6 in blood is aberrantly high in heatstroke cases (Shigeto Oda, Journal of the Japanese Society of Intensive Care Medicine, 2008; 15: 166-167).

The present invention will be described in more detail.

1. Active Ingredient

The "auraptene" is a compound classified into coumarins and is also called 7-geranyloxycoumarin, etc. The compound has the following structural formula.

[Formula 1]

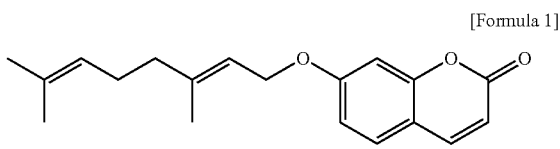 [SMILES: CC(C)=CCC/C(C)=C/COc1ccc2ccc(=O)oc2c1]

The auraptene may be extracted or purified from a plant material, or may be artificially synthesized (such a product is referred to as a synthetic substance).

The plant material is not particularly limited as long as the plant material contains auraptene. Preferred examples thereof include fruits of citruses. A fruit (which is not limited by its variety) of at least one citrus selected from *Citrus natsudaidai, Citrus hassaku, Citrus x paradisi, Citrus junos, Citrus sphaerocarpa*, and *Citrus grandis* is more preferred. The skins of these fruits are rich in auraptene, and the auraptene can be efficiently obtained by using these fruits as plant materials.

Alternatively, the auraptene can be obtained at a yield of approximately 65% by reacting 7-hydroxycoumarin with trans-geranyl bromide in the presence of DBU in acetone at room temperature for approximately 1 day, followed by purification by silica gel column chromatography (eluent, petroleum ether:ethyl acetate=9:1 (v/v)) (M. Askari et al., Iran J Basic Med Sci 2009, 12 (2): 63-69).

The "tangeretin" is a polymethoxyflavonoid compound and is also called 4',5,6,7,8-pentamethoxyflavone. The compound has the following structural formula.

[Formula 2]

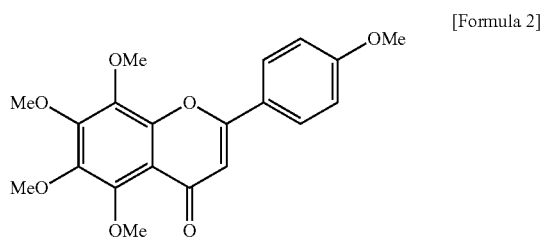 [SMILES: COc1ccc(-c2cc(=O)c3c(OC)c(OC)c(OC)c(OC)c3o2)cc1]

The tangeretin may be extracted or purified from a plant material, or may be artificially synthesized (such a product is referred to as a synthetic substance).

The plant material is not particularly limited as long as the plant material contains tangeretin. Preferred examples thereof include fruits of citruses. A fruit (which is not limited by its variety) of at least one citrus selected from *Citrus reticulata* and *Citrus depressa* is more preferred. The skins of these fruits are rich in tangeretin, and the tangeretin can be efficiently obtained by using these fruits as plant materials.

Alternatively, the tangeretin can be obtained by reacting 2'-hydroxy-3',4',5',6'-tetramethoxyacetophenone with 3-methoxybenzaldehyde in the presence of a 14% aqueous potassium hydroxide solution in ethanol at room temperature to synthesize 2'-hydroxy-3',4',5',6',3-pentamethoxychalcone, further heating the obtained product to reflux in the presence of sodium ethoxide in ethanol to synthesize 5,6,7,8,3'-pentamethoxy-flavanone, and subsequently performing oxidation reaction in the presence of DDQ in dioxane, followed by purification by silica gel column chromatography or the like (e.g., S-I Cai et al., Chem Res Chinese Universities 2012, 28 (4): 631-636).

The "medium chain fatty acid" is a fatty acid having 6 to 12 carbon atoms (medium chain) and includes, for example, C6 caproic acid, C8 caprylic acid, C10 capric acid, and C12 lauric acid. The "medium chain fatty acid" as used herein can include medium chain fatty acid glyceride, for example, MCT (medium chain triglyceride), which is degraded in vivo to form medium chain fatty acid. MCT is a triglyceride oil composed mainly of medium chain fatty acid (e.g., approximately 60% to 100%).

For example, coconut oil contains approximately 60% of medium chain fatty acids comprising 7.5% caprylic acid (C8), 6.0% capric acid (C10), and 45% lauric acid (C12). MCT oil consisting essentially of caprylic acid (C8) or capric acid (C10) is liquid, whereas coconut oil is in a solid state at 20° C. or lower, in a cream state at 20° C. to 25° C., and in a liquid state at 25° C. or higher.

The medium chain fatty acid is relatively soluble in water and therefore eliminates the need of preparing micelles with bile acid. The medium chain fatty acid is easily absorbed into small intestinal absorptive cells, and absorbed into intestinal capillaries because of its small molecule. Unlike long chain fatty acid, the medium chain fatty acid is neither resynthesized into neutral fat nor forms chylomicron and is delivered in the form of free fatty acid to the liver through the portal vein and easily metabolized rapidly as an energy source.

The medium chain fatty acid is reportedly absorbed approximately 4 times faster and metabolized 5 to 10 times faster than long chain fatty acid. Since the energy utilization rate of the medium chain fatty acid is fast, its effect of prolonging the duration of heavy exercise has also been reported. Furthermore, experimental results in animals or humans indicate that neutral fat of medium chain fatty acid is less likely to cause obesity as compared to fat comprising long chain fatty acid. Coconut oil comprises approximately 50% lauric acid as medium chain fatty acid, and people of South Asian or Oceanian regions who consume a lot of coconut oil reportedly have a low incidence of disease of the cardiovascular system.

The composition of the present invention can comprise a synthetic substance or a substance derived from an extract of a plant material, for example, a form of an extract or a form purified from the extract, as the at least one substance selected from the group consisting of auraptene, tangeretin and medium chain fatty acid.

The "form of an extract" means a fraction containing auraptene, tangeretin, or medium chain fatty acid, separated or obtained from the plant material. Examples of the "extract" can include squeezes, extracts, and mixtures thereof, and concentrates or dry products obtained by concentrating or drying the squeezes, the extracts, or the mixtures thereof.

The "squeeze" can be prepared by homogenizing and pressing the plant material, and separating a liquid fraction from a solid fraction such as cell walls to obtain the liquid fraction. The separation of the liquid fraction from the solid fraction can be performed by a usual solid-liquid separation technique such as centrifugation or filtration.

The "extract" can be prepared by extracting the component of interest from the plant material with an extraction medium. A solvent generally used for the extraction of auraptene or tangeretin can be utilized as the extraction medium (JP Patent Publication (Kokai) No. 11-29565 A (1999), JP Patent Publication (Kokai) No. 2009-215318 A (2009), etc.). Water, ethanol, methanol, isopropanol, propylene glycol, diethyl ether, hexane, acetone, acetonitrile, ethyl acetate, or a mixture of two or more of these solvents can be utilized as such an extraction solvent. In the case of producing the extract by solvent extraction, each plant material is dipped in an appropriate amount of the solvent (e.g., an amount of 0.5 to 20 times the weight of the plant material), and appropriately stirred or left standing to elute a solvent-soluble component into the solvent. The extraction time is not particularly limited and can be appropriately selected from 5 minutes to 1 week. The extraction temperature is not particularly limited and can be set to 0° C. to 125° C., for example, 25° C. to 125° C. A solvent fraction containing the solvent soluble component thus extracted is separated from a solid fraction such as cell walls by the solid-liquid separation technique mentioned above to obtain the solvent fraction as the extract. The form of each plant material for use in the extraction can be its original form, or a state cut into an appropriate size or shape, or a form of a dry product, a homogenate, or a squeeze.

The obtained extract may be further subjected, if necessary, to a purification technique such as solvent fractionation, use of an adsorbent for chromatography (column chromatography, high-performance liquid chromatography (HPLC), supercritical carbon dioxide chromatography, etc.) and/or recrystallization to separate or purify the component of interest (JP Patent Publication (Kokai) No. 11-29565 A (1999), JP Patent Publication (Kokai) No. 2004-35709 A (2004), WO2014/057727, etc.). The purification may be, for example, partial purification or complete purification which gives the component of interest with a purity of approximately 1% to 100%.

The "concentrate or dry product" can be produced by concentrating or drying the squeeze or the extract, or a mixture thereof. In this context, the concentration refers to decreasing the amount of a liquid (water and/or the extraction solvent) in the squeeze or the extract, or the mixture thereof. The degree of concentration can be determined, for example, by using a sugar content (Bx) or an acidity as an index. The sugar content can be measured with a commercially available sugar content meter, and the acidity can be measured by a neutralization titration method. For example, vacuum evaporative concentration or membrane concentration can be adopted as a concentration method. The vacuum evaporative concentration is generally called concentration under reduced pressure. The membrane concentration can be performed using, for example, a membrane such as a reverse osmosis membrane (RO) or an ultrafiltration membrane (UF). The type of the membrane used can be selected within a range that permits, for example, a sugar content of approximately 50% or more, and is not particularly limited. The drying can be carried out by drying the squeeze or the extract, or the mixture thereof by use of the usual drying technique described above. For the concentration or the drying, the squeeze, the extract, or the concentrate may be concentrated or dried in combination with an additional component such as an excipient.

2. Composition and Use Thereof

The composition of the present invention can be appropriately supplemented with an additional component(s) (also referred to as an additive(s)), for example, an excipient, an extender, a disintegrant, a lubricant, a binder, an antioxidant, a colorant, an anti-aggregation agent, an absorption promoter, a solvent, a solubilizer, a tonicity agent, a stabilizer, a corrigent, an antiseptic, and/or a pH adjuster, acceptable as a pharmaceutical or a food or drink or acceptable as animal feed or a feed additive, selected according to the desired form for the composition, in addition to the at least one substance selected from the group consisting of auraptene, tangeretin and medium chain fatty acid as an active ingredient.

The composition of the present invention can further comprise an additional substance effective for preventing, alleviating and/or treating a heat illness. Examples of such a substance include, but are not limited to, minerals (sodium, potassium, etc.), carnitine (WO2013/005403), α-linolenic acid (JP Patent Publication (Kokai) No. 2016-37498 A (2016)), egg white peptides (JP Patent Publication (Kokai) No. 2008-72968 A (2008)), and sake cake and malted rice (JP Patent Publication (Kokai) No. 2007-001937 A (2007)).

The composition of the present invention can be provided in the form of a medicament (including a quasi-drug) or a food or drink (i.e., a beverage or a food product except for beverages) or in the form of animal feed or a feed additive.

As used herein, the "subject" is a homeothermic animal such as bird or a mammal, preferably a human, a livestock animal, a pet animal, or the like, particularly preferably a human. The livestock animal comprises economically important animals, such as cattle, pigs, and chickens, known to suffer enormous damage on, for example, milk or meat production, chicken egg production, or breeding due to heat stress. The pet animal comprises animals, such as dogs, cats, rabbits, squirrels, and hamsters, kept in the house. When the subject is a human, every human is intended, and examples thereof include, but are not limited to, elderly people and infants who are especially susceptible to heat stress, and people who work, do activities, do exercise, or live in high-temperature environments.

The dosage form (oral or parenteral dosage form) of the medicament is not particularly limited and is preferably a form suitable for oral administration. Examples of a solid composition for oral administration (solid pharmaceutical preparation) can include forms such as tablets (including sugar-coated tablets), pills, capsules, powders, fine granules, granules, troches, chewables, and lozenges. Examples of a liquid composition for oral administration (liquid pharmaceutical preparation) can include forms such as emulsions, solutions, suspensions, and syrups. Alternatively, examples of a composition for parenteral administration can include forms such as emulsions for intravenous administration and suppositories for transrectal administration. These preparations can be formulated in accordance with a routine method by appropriately blending the at least one substance selected from the group consisting of auraptene, tangeretin and medium chain fatty acid, with the additional component (additive) according to the dosage form.

Examples of the form of the food or drink include, but are not particularly limited to, candies, tablets, refreshing drinks (e.g., carbonated beverages, fruit beverages, coffee beverages, tea-based beverages, mineral water, soymilks, vegetable beverages, isotonic drinks, and lactic beverages), jelly beverages, and food products (e.g., seasonings, confectionery, bread, cake, ice creams, ice confectionery, dairy products, meat products, fish meat products, fruit vegetable products, fruit products, fermented food products, and food additives). The food or drink includes general foods or drinks as well as health foods, foods with health-promoting benefits, foods with nutrient function claims, foods for specified health use, foods for the sick, etc. These foods or drinks can have an indication that states having an effect such as the prevention of a heat illness or measures against a heat illness.

The form of the animal feed or the feed additive is not particularly limited, and the animal feed or the feed additive is prepared in an oral dosage form or a form suitable for oral provision, such as powders, granules, pellets, pills, or sticks. The animal feed or the feed additive can be formulated in accordance with a routine method by appropriately blending the at least one substance selected from the group consisting of auraptene, tangeretin and medium chain fatty acid with a usual dietary component suitable for the type of the subject according to the dosage form. The feed or the feed additive can be appropriately supplemented with, for example, cereals (e.g., cereal flour and grains) such as corn, beans, rice, and wheat or barley as well as a component, for example, amino acids, vitamins, minerals, probiotics (lactic acid bacteria, bifidobacteria, yeasts, etc.), and emulsifiers, which are substances for addition to feed designated by regulatory authorities.

The composition of the present invention can be used for preventing, alleviating and/or treating a heat illness.

As used herein, the "heat illness" means a generic name for heat syncope, heat cramp, heat exhaustion, and heatstroke, as well as health disorders including syncope caused by elevation of body temperature ascribable to a high-temperature bath (heat syncope), shock or disturbance of consciousness (heatstroke) (Guidelines for Diagnosis and Management of Syncope, p. 37-39 (JCS 2012, The Japanese Circulation Society), etc.

In the present invention, the phrase "prevent, alleviate and/or treat a heat illness" includes preventing, alleviating and/or treating a heat illness based on cytotoxicity by preventing, alleviating and/or treating, for example, the cytotoxicity, such as disturbance of metabolism, dysfunction, or cell death, of cells such as vascular endothelial cells, brain neurons, or muscular cells (e.g., striated muscle cells) resulting from the load of heat stress, disorder of organs such as blood vessels, the brain, or muscles caused thereby, and/or aberration (e.g., fever and high body temperature) associated with the production and release of a fever-inducing inflammatory cytokine(s) from blood cells (e.g., lymphocytes and leukocytes) caused by the load of heat stress, and thereby preventing or improving a lack of oxygen or poor nutrition in tissues or cells derived from such disorder of organs.

The "heat stress" means, for example, temperature conditions of higher than 37° C., for example, 38° C., 39° C., 40° C., 41° C., 42° C., 43° C., 44° C., 45° C. or higher, to which cells such as vascular endothelial cells, brain neurons, or muscular cells are exposed. In the case of a human, the risk of causing cytotoxicity is elevated when the body temperature exceeds 40° C. On the other hand, in the case of a non-human subject, for example, a pig, cytotoxicity is found when the body temperature exceeds 42° C. Thus, the temperature at which heat stress has influence varies somewhat depending on the type of the subject. In such a case, it is also known that the body temperature or body fluid regulatory function of the body is damaged in association with change in environmental conditions such as elevation of temperature or humidity so that the symptoms of a heat illness as described above occur.

Examples of the "cytotoxicity" include, but are not particularly limited to, the cytotoxicity of cells such as vascular endothelial cells, brain neurons, or muscular cells resulting from the load of heat stress. Specific examples of the cytotoxicity include reduced metabolism (e.g., reduced lipid metabolism), increased amounts of pyrogenic factors, the reduced ability of cells to proliferate, and cell death.

Examples of the "heat illness symptom based on tissue or cell dysfunction" include, but are not particularly limited to, symptoms that are generally found in a heat illness. Specific examples thereof include dizziness, syncope, facial pallor, muscle soreness, cramps, muscle spasm, heavy sweating, general malaise or sinking feeling, headache, nausea, vomiting, impaired concentration or judgement, high body temperature, disturbance of consciousness, general convulsion, disturbance of limb motility, and tissue damage.

The at least one substance selected from the group consisting of auraptene, tangeretin and medium chain fatty acid as an active ingredient in the composition of the present invention suppresses the cytotoxicity including cell death, etc. Specifically, as shown in Examples mentioned later, these components increase or enhance the lipid metabolism of cells such as vascular endothelial cells (decrease the amount of intracellular fat droplets or increase the expression of PPARα and PPARγ) caused by the load of heat stress, suppress the production of a fever-inducing inflammatory cytokine(s) (pyrogenic factor(s)), and suppress the cytotoxicity, including cell death, of vascular endothelial cells. Therefore, these components are effective for preventing, alleviating and/or treating a heat illness, or the cytotoxicity of vascular endothelial cells caused by the load of heat stress and/or aberration (e.g., fever and high body temperature) associated with the production and release of a fever-inducing inflammatory cytokine(s) caused by the load of heat stress.

Heat stress is a possible cause of the heat illness. In general, the elevated degree of heat stress increases the risk of the heat illness. As shown in Examples mentioned later, the heat stress is responsible for the inhibition of cell proliferation of vascular cells, particularly, vascular endothelial cells and induces cytotoxicity such as cell death. When blood vessels undergo the load of heat stress, blood cells also undergo the load of heat stress, as in the blood vessels. In this respect, inflammatory cytokines (e.g., IL-6 and CCL2) are released from the blood cells (e.g., lymphocytes), damaging or influencing cells such as vascular endothelial cells. As shown in Examples mentioned later, the at least one substance selected from the group consisting of auraptene, tangeretin and medium chain fatty acid suppresses or alleviates, for example, the cytotoxicity of cells such as vascular cells (e.g., vascular endothelial cells) placed under heat stress load and aberration (e.g., fever and high body temperature) associated with the production and release of a fever-inducing inflammatory cytokine(s) from blood cells, and is therefore capable of preventing, alleviating and/or treating a heat illness.

Thus, the composition of the present invention has, as also described in Examples mentioned later, at least one effect selected from the group consisting of an effect of suppressing the cytotoxicity of vascular endothelial cells caused by the load of heat stress, an effect of increasing or enhancing lipid metabolism, and an effect of decreasing the production and release of a fever-inducing inflammatory cytokine(s) from blood cells caused by the load of heat stress, preferably all of the effects.

The amount of the composition of the present invention to be administered or provided varies depending on factors such as the age, body weight, sex, and symptoms of the recipient subject, or an administration route and is not particularly limited. The amount is, for example, approximately 0.04 mg or larger, approximately 0.1 mg or larger, approximately 0.5 mg or larger, or approximately 1 mg or larger, in terms of the amount of the active ingredient (dose of auraptene, tangeretin or medium chain fatty acid), for example, per administration or provision per kg of the body weight of the subject including a human. Alternatively, the amount of the composition of the present invention to be administered or provided may be, for example, approximately 0.05 mg to approximately 5000 mg or larger, approximately 0.1 mg to approximately 1000 mg or larger, or approximately 1 mg to approximately 500 mg or larger, in terms of the amount of the active ingredient per day. Also, the composition of the present invention can be administered or provided once or a plurality of times a day. The "plurality of times" mean two or more times and mean, for example, but are not particularly limited to, 2, 3, 4, 5, 6 or more times.

The present invention provides a method for preventing, alleviating and/or treating a heat illness, or cytotoxicity of cells such as vascular endothelial cells, brain neurons, or muscular cells caused by the load of heat stress and/or aberration (e.g., fever and high body temperature) associated with the production and release of a fever-inducing inflammatory cytokine(s) from blood cells caused by the load of heat stress in a subject, comprising administering or providing the composition to the subject. The composition is capable of preventing the heat illness by administration or provision at the dose described above to, for example, a subject susceptible to heat stress or possibly undergoing the stress. Alternatively, the composition is capable of alleviating or improving symptoms of the heat illness by administration or provision at the dose described above to a subject that has undergone heat stress or manifests the symptoms of the heat illness. In this respect, further hydration or supplementation with an electrolyte would produce the preventing or improving effect described above.

The present invention further provides use of at least one substance selected from the group consisting of auraptene, tangeretin and medium chain fatty acid for the production of a composition for preventing, alleviating and/or treating a heat illness in a subject, and use of at least one substance selected from the group consisting of auraptene, tangeretin and medium chain fatty acid in a composition for preventing, alleviating and/or treating the cytotoxicity of cells such as vascular endothelial cells, brain neurons, or muscular cells caused by the load of heat stress and/or aberration (e.g., fever and high body temperature) associated with the production and release of a fever-inducing inflammatory cytokine(s) from blood cells caused by the load of heat stress in a subject, or use thereof for the production of the composition.

The composition can have any of various forms and amounts of the active ingredient described above depending on its use. For the production of the composition, a predetermined amount of the at least one substance selected from the group consisting of auraptene, tangeretin and medium chain fatty acid as an active ingredient can be blended with an excipient, a food or drink, or feed and, optionally, an additive(s) to formulate or process into a shape or a form for the use of interest.

Hereinafter, the present invention will be described with reference to Examples in more detail. However, the present invention is not limited by these Examples.

EXAMPLES

Example 1

<Suppression of Cytotoxicity of Vascular Endothelial Cells Under Heat Stress Load by Auraptene and Tangeretin>
1. Material
(1) Human Normal Cell Line
Human umbilical vein vascular endothelial cells (HUVECs: purchased from Kurabo Industries Ltd. (Japan)) were used in this Example.
(2) Cell Culture Medium
To 500 mL of HuMedia-EB2 (Kurabo Industries Ltd.), 10 mL of fetal bovine serum (FBS) was added, and 500 µL each of an auxiliary factor attached to the culture kit, hEGF, hydrocortisone, an antimicrobial agent(s), hFGF-B, and heparin was added, and the resulting medium was used as a HUVEC culture medium.

To RPMI-1640 (Sigma-Aldrich Co. LLC), 50 mL of FBS was added, and 5 mL each of GlutaMAX (Gibco), Na-Pyruvate (Gibco), and Pen-Strep (Gibco) was added, and the resulting medium was used as a lymphocyte culture medium.
(3) ELISA Kit
Human IL-6 (BioLegend, Inc.) and Human MCP1/CCL2 (BioLegend, Inc.) were used for measuring inflammatory cytokine concentrations in a lymphocyte supernatant.
(4) Antibody Used
An anti-PPARα antibody (Cell Signaling Technology, Inc.), an anti-PPARγ antibody (Cell Signaling Technology, Inc.), an anti-CPT-11 antibody (Atlas Antibodies), an anti-ABCD3 antibody (Atlas Antibodies), BODIPY (Thermo Fisher Scientific Inc.) and MitoSpy-Green (BioLegend, Inc.) were used for confirming change in the expression of proteins related to heat stress resistance and lipid metabolism of vascular endothelial cells. For fluorescent antibodies, DyLight 649-labeled anti-Mouse IgG antibody (Rockland Immunochemicals, Inc.) and DyLight 649-labeled anti-Rabbit IgG antibody (Rockland Immunochemicals, Inc.) were used as secondary antibodies.
(5) Fluorescent Dye Used
$DiOC_6$ (Invitrogen Corp.) and PI (Sigma-Aldrich Co. LLC) were used as fluorescent dyes for measuring cell death.
(6) Phytochemical
A pharmacological or physiological effect research reagent ergothioneine (Wako Pure Chemical Industries, Ltd. (Japan)), nobiletin (Wako Pure Chemical Industries, Ltd.), a component auraptene (Wako Pure Chemical Industries, Ltd.), and tangeretin (Wako Pure Chemical Industries, Ltd.) were used as heat stress-resistant components in this experiment. Ergothioneine was dissolved in 1×PBS to adjust its concentration to 5 mg/mL. Nobiletin, auraptene, or tangeretin was dissolved in dimethyl sulphoxide (DMSO; Sigma-Aldrich Co. LLC) to adjust its concentration to 1 mM. Each solution was preserved at −20° C.
2. Experiment and Results
(1) Morphological Change of Vascular Endothelial Cells Under Heat Stress Load
A supernatant of human vascular endothelial cells (HUVECs) cultured in a 10-cm dish was removed with an aspirator. Then, 2 mL of trypsin/EDTA was added to the cells, and the cells were detached by incubation at 37° C. in a 5% $CO_2$ environment. After the cell detachment, 5 mL/dish of a culture medium was added, and the cells were transferred to a 15-mL tube and centrifuged at 1200 rpm for 5 minutes in a centrifuge. The supernatant was removed, and then, the number of cells was adjusted to a cell density of $5 \times 10^4$ cells/mL using a cell counting kit by the addition of 5 mL of a culture medium. Then, the solution with the adjusted HUVEC density was inoculated at 4 mL/dish to 5 wells of each 6-well plate, incubated at 37° C. for 1 day in 5% $CO_2$, and 1 day later, incubated at 40° C. for 3 days in the presence of 5% $CO_2$.

The supernatant of the HUVECs cultured in the 6-well plate was removed, and 2 mL/dish of 4% paraformaldehyde in a phosphate buffer solution was added. The cells were left standing at room temperature for 1 hour for cell fixation. The solution was removed, and then, the cells were rinsed twice. Crystal violet (CV; Kishida Chemical Co., Ltd. (Japan)) was added at 1 mL/well, and the cells were left standing overnight at 37° C. The solution was removed, and then, 1×PBS was added to the cells, followed by photographing under a phase contrast microscope.

As a result of phase contrast microscopic observation, change in shape was seen in the human vascular endothelial cells (HUVECs) cultured under heat stress load at 40° C. as compared to usual culture, and the three-dimensional structures of the cells were weakened, confirming cell proliferation impaired due to the load of heat stress. Furthermore, the shrinkage of the cells caused the formation of space between the cells, whereby decrease in cell density, thus decrease in the number of cells, was observed (FIGS. 1A and 1B).

(2) Change in Amount of ATP Produced in Vascular Endothelial Cells Under Heat Stress Load The CV staining qualitatively confirmed that the number of human vascular endothelial cells (HUVECs) was decreased by culturing the cells at 40° C. Therefore, the amount of ATP was measured for quantitative evaluation.

In the same way as in the preceding section (1), vascular endothelial cells (HUVECs) were cultured in an environment of 37° C. or 40° C., and 3 days later, the amount of ATP produced was measured for the cells. The intracellular ATP measurement was conducted using Cell ATP Assay Reagent (Toyo B-Net Co., Ltd. (Japan)). The method was carried out in accordance with the instruction manual. The amount of ATP was measured as the amount of luminescence by luciferase assay using a microplate reader.

As a result, it was confirmed that the amount of ATP produced is decreased by 70% or more (FIG. 2).

(3) Analysis on Localization of CPT-II in Vascular Endothelial Cells Placed Under Heat Stress Load A supernatant of human vascular endothelial cells (HUVECs) cultured in a 10-cm dish was removed with an aspirator. Then, 2 mL of trypsin/EDTA was added to the cells, and the cells were detached by incubation at 37° C. in a 5% $CO_2$ environment. After the cell detachment, 5 mL/dish of a culture medium was added, and the cells were transferred to a 15-mL tube and centrifuged at 1200 rpm for 5 minutes in a centrifuge. The supernatant was removed, and then, the number of cells was adjusted to a cell density of $5 \times 10^4$ cells/mL using a cell counting kit by the addition of 5 mL of a culture medium. Then, a 35-mm dish was provided, and 2 mL/dish of the solution with the adjusted HUVEC density was inoculated, incubated at 37° C. for 1 day in the presence of 5% $CO_2$, and 1 day later, cultured at 37° C. or 40° C. in an incubator.

The supernatant was removed after 3-day culture, and 2 mL/dish of 4% paraformaldehyde in a phosphate buffer solution was added. The cells were left standing at room temperature for 1 hour. The solution was removed, and then, the cells were rinsed twice. 2 mL/dish of 0.5% Triton-X100 (Wako Pure Chemical Industries, Ltd.) in PBS was added, and the cells were left standing at room temperature for 5 minutes. The solution was removed, and then, the cells were rinsed twice. 1 mL/dish of an anti-CPT-II antibody (rabbit) diluted 500-fold with a FACS buffer was added, and the cells were left standing at room temperature for 2 hours for reaction.

The solution was removed, and then, the cells were rinsed twice. 1 mL/dish of DyLight 649-labeled anti-Rabbit IgG antibody diluted 500-fold with a FACS buffer was added, and the cells were left standing at room temperature for 1 hour in the dark for reaction. The solution was removed, and then, the cells were rinsed twice. Two drops of Diamond Antifade Mountant with DAPI were added to the cells, and a round glass cover was put on the cells, followed by fluorescence photographing under a confocal laser scanning microscope.

Figure 3A:
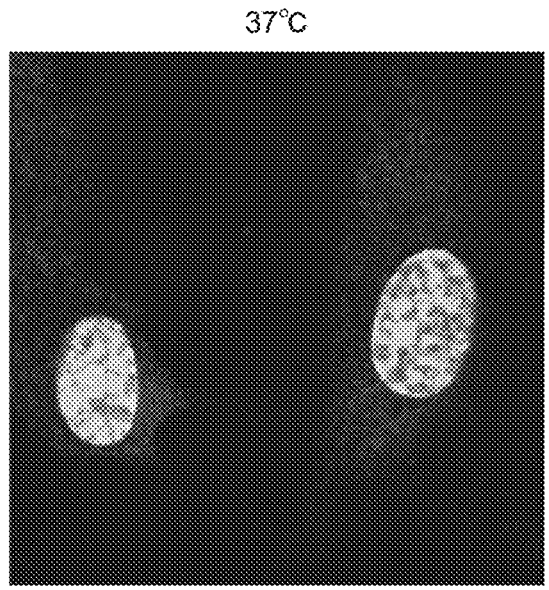
FIGS. 3A and 3B show confocal laser scanning micrographs of cells that exhibit change in CPT-II expression caused by the load of heat stress. When human vascular endothelial cells (HUVECs) are cultured at 40° C. for 3 days, the expression of CPT-II, an enzyme transporting long chain fatty acids into mitochondria, is decreased (FIG. 3B). Results of measuring the CPT-II expression of HUVECs after culture at 37° C. for 3 days are shown as a comparative control (FIG. 3A). In this context, the CPT-II expression in the cells was measured using Alexa 647-anti-CPT-II antibody.
Figure 3B:
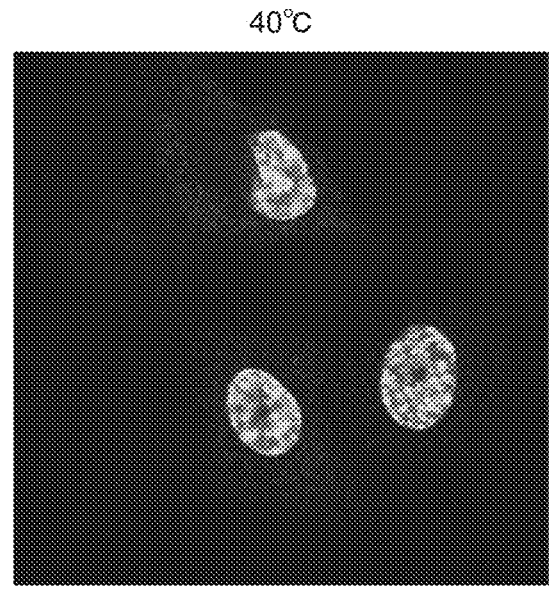

As a result of analyzing change in the expression level of CPT-II in human vascular endothelial cells (HUVECs) under heat stress load using the fluorescent antibody reaction method and a confocal laser scanning microscope, it was confirmed that the expression level of CPT-II was decreased in the cells cultured under heat stress load (40° C.) as compared to the cells cultured under usual conditions (37° C.), because CPT-II is a thermolabile enzyme (FIGS. 3A and 3B).

(4) Analysis on Localization of Mitochondria in Vascular Endothelial Cells Placed Under Heat Stress Load The cell density of human vascular endothelial cells (HUVECs) cultured in a 10-cm dish was adjusted to $5 \times 10^4$ cells/mL. Then, a 35-mm dish was provided, and 2 mL/dish of the solution with the adjusted HUVEC density was inoculated, incubated at 37° C. for 1 day in the presence of 5% $CO_2$, and 1 day later, cultured at 37° C. or 40° C. in an incubator.

Three days later, MitoSpy-Green solution (250 nM) was added to the cultured vascular endothelial cells, and the cells were further cultured for 1 hour. Then, the culture supernatant was removed, and 2 mL/dish of 4% paraformaldehyde in a phosphate buffer solution was added. The cells were left standing at room temperature for 1 hour. The solution was removed, and then, the cells were rinsed twice. 2 mL/dish of 0.5% Triton-X100 (Wako Pure Chemical Industries, Ltd.) in PBS was added, and the cells were left standing at room temperature for 5 minutes. Then, two drops of Diamond Antifade Mountant with DAPI were added to the cells, and a round glass cover was put on the cells, followed by fluorescence photographing under a confocal laser scanning microscope.

Figure 4A:
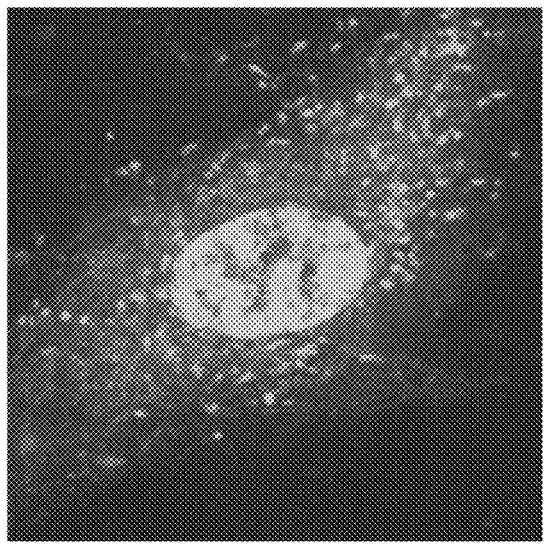
FIGS. 4A and 4B show confocal laser scanning micrographs showing reduction in intracellular mitochondrial activity caused by the load of heat stress. Decrease in the amount of intracellular mitochondria is shown, wherein human vascular endothelial cells (HUVECs) were cultured at 40° C. for 3 days, and the mitochondria were stained with MitoSpy-Green (FIG. 4B). Results of measuring the mitochondrial activity of HUVECs after culture at 37° C. for 3 days are shown as a comparative control (FIG. 4A).
Figure 4B:
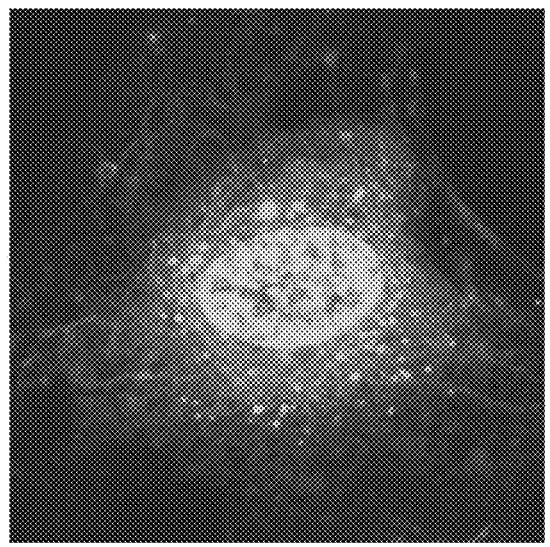

As a result of analyzing change in the amount of mitochondria in human vascular endothelial cells (HUVECs) placed under heat stress load by MitoSpy-Green staining, the presence of many mitochondria dispersed in the cytoplasms was observed in the HUVECs cultured at 37° C. By contrast, mitochondria were gathered near the nuclei without being dispersed in the cytoplasms, in the HUVECs cultured at 40° C., and the amount of the mitochondria was also decreased (FIGS. 4A and 4B). This was consistent with the decreased amount of ATP produced in the preceding section (2).

(5) Suppression of Cytotoxicity of Vascular Endothelial Cells Under Heat Stress Load by Addition of Phytochemical A supernatant of human vascular endothelial cells (HUVECs) cultured in a 10-cm dish was removed with an aspirator. Then, 2 mL of trypsin/EDTA was added to the cells, and the cells were detached by incubation at 37° C. in a 5% $CO_2$ environment. After the cell detachment, 5 mL/dish of a culture medium was added, and the cells were transferred to a 15-mL tube and centrifuged at 1200 rpm for 5 minutes in a centrifuge. The supernatant was removed, and then, the number of cells was adjusted to a cell density of $5\times10^4$ cells/mL using a cell counting kit by the addition of 5 mL of a culture medium. Then, two 6-well plates were used, and the solution with the adjusted HUVEC density was inoculated at 4 mL/well to 3 wells of each plate. Each phytochemical component was added at 4 µL (final concentration: 10 µM)/well to one well of each plate. Also, a phytochemical dissolving solution DMSO was added at 4 µL/well to the remaining wells to prepare a control. The cells were incubated at 37° C. for 1 day in the presence of 5% $CO_2$, and 1 day later, the plates were incubated at 37° C. and 40° C., respectively, for 2 days in 5% $CO_2$.

Two days later, the culture solution of each well was removed with an aspirator. 2 mL of trypsin/EDTA was added to the cells, and the cells were detached by incubation at 37° C. in a 5% $CO_2$ environment. After the cell detachment, 5 mL/dish of a culture medium was added, and the cells were transferred to a 15-mL tube and centrifuged at 1200 rpm for 5 minutes in a centrifuge. The supernatant was removed, and then, 5 mL of a culture medium at 37° C. was added to the cells and stirred. After the stirring, $DiOC_6$ (final concentration: 80 nM) was added to each 15-mL tube and reacted at the same temperature as the culture temperature for 30 minutes.

The cells thus reacted were centrifuged at 1200 rpm for 5 minutes in a centrifuge. The supernatant was removed, and then, 1 mL of a culture medium was added to the cells, and 2 µL of PI (Sigma-Aldrich Co. LLC) was added. The cells thus supplemented were transferred to a FACS tube and measured in a flow cytometer (BD).

Figure 5:
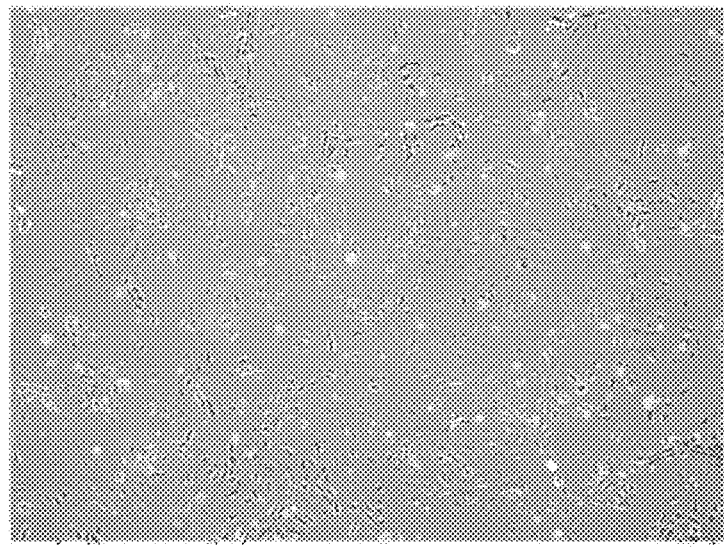
FIG. 5 shows a phase contrast micrograph of human vascular endothelial cells (HUVECs) when the cells were cultured at 40° C. for 2 days in only a medium. From the figure, many dead cells are observed.
Figure 6:
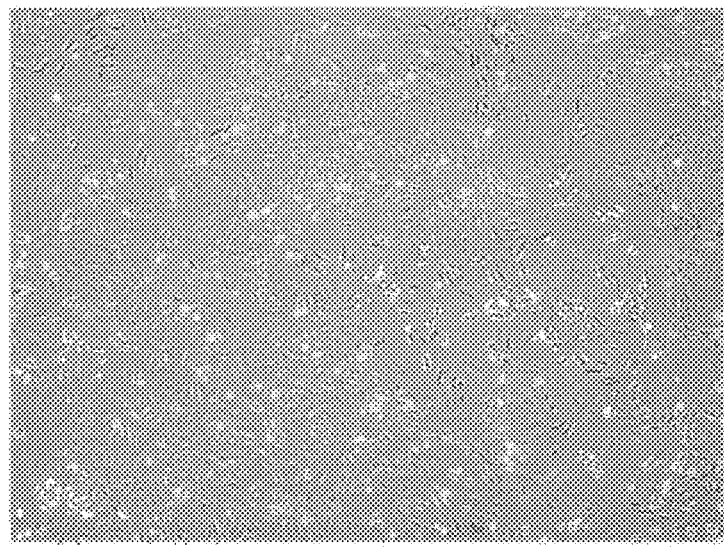
FIG. 6 shows a phase contrast micrograph of human vascular endothelial cells (HUVECs) when the cells were cultured at 40° C. for 2 days in a tangeretin-containing medium. As compared to FIG. 5 (control), decreased dead cells and increased live cells are observed.
Figure 7:
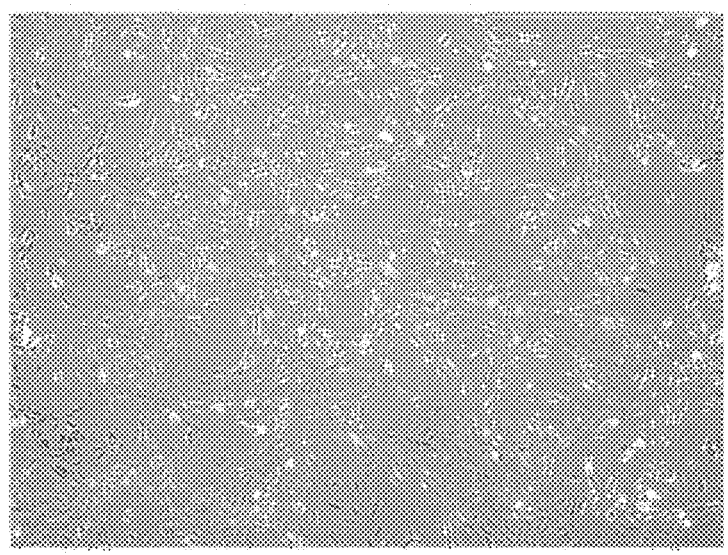
FIG. 7 shows a phase contrast micrograph of human vascular endothelial cells (HUVECs) when the cells were cultured at 40° C. for 2 days in an auraptene-containing medium. As compared to FIG. 5 (control), decreased dead cells and increased live cells are observed.

As a result of phase contrast microscopic observation, auraptene and tangeretin were found as components capable of suppressing the cytotoxicity of human vascular endothelial cells (HUVECs) caused by the load of heat stress, and HUVECs cultured by the addition of each of these components exhibited evidently increased survival (FIGS. 5 to 7). In this respect, the non-addition of the substance (active ingredient) was used for a negative control. Although not shown in the figures, the addition of the PPAR agonist bezafibrate as well as ergothioneine, nobiletin, osthol, resveratrol, or sulforaphane was unable to suppress the cytotoxicity caused by heat stress. In particular, nobiletin, which is polymethoxyflavonoid very structurally similar to tangeretin (except that the number of methoxy groups is larger by one than that of the tangeretin), did not have the suppressive effect as described above.

Figure 8C:
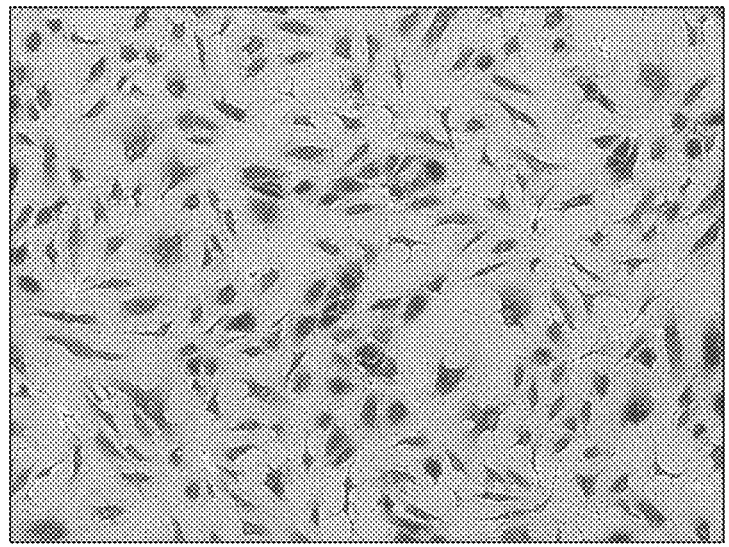
FIGS. 8A, 8B and 8C show the heat stress resistant effects of auraptene and tangeretin when human vascular endothelial cells (HUVECs) were cultured at 40° C. for 3 days (FIGS. 8B and 8C, respectively). Culture in a DMSO-containing medium was used for a control (FIG. 8A). In this context, the cells were stained with crystal violet and photographed under a phase contrast microscope.
Figure 8B:
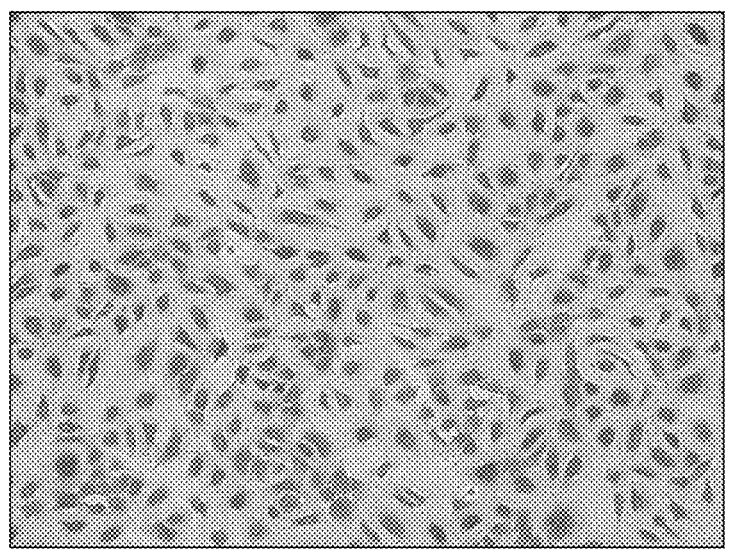
Figure 8A:
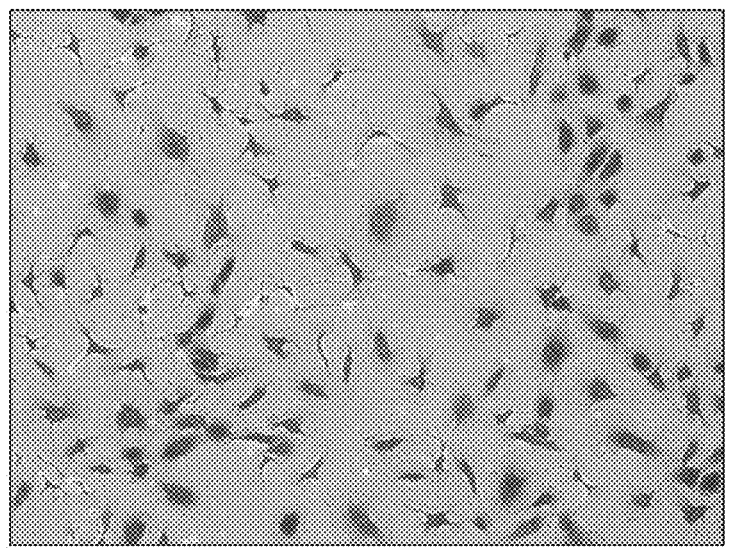

In order to further confirm the cytotoxicity suppressive effects of auraptene and tangeretin, the cells cultured at 40° C. were observed by crystal violet staining. As a result, marked cytotoxicity was confirmed in the addition of a solvent DMSO, whereas evidently increased cell survival was observed in the addition of auraptene and tangeretin (FIGS. 8A, 8B and 8C).

Figure 9:
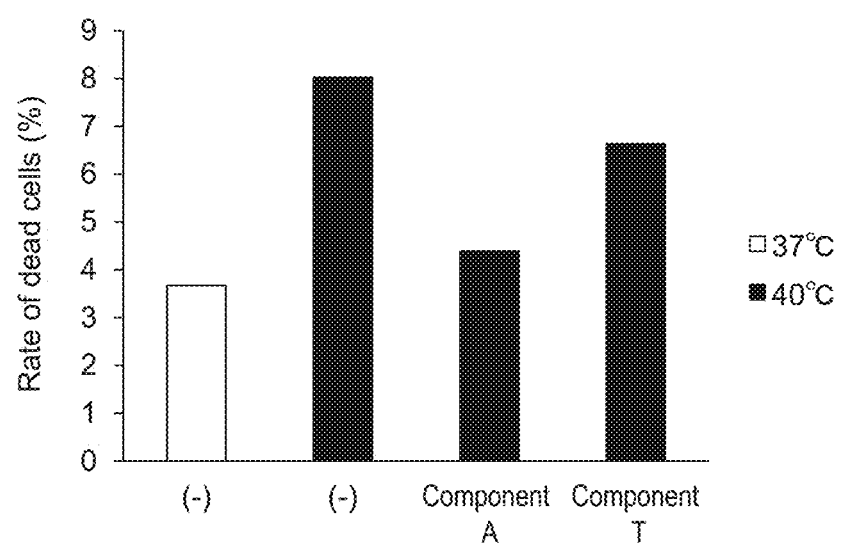
FIG. 9 shows results of quantifying effects of increasing $DiOC_6$ staining-positive cells and suppressing cytotoxicity (cell death) by the addition of auraptene (component A) or tangeretin (component T) when human vascular endothelial cells (HUVECs) were cultured under heat stress load at 40° C. for 2 days. Cell culture in a medium containing no component at 37° C. or 40° C. was used for a control. Dead cells were quantified by PI staining.

In order to quantify the effects, the cytotoxicity suppressive effects of auraptene (component A) and tangeretin (component T) inhibiting the cell death caused by the load of heat stress were quantified using DiOC6 staining and flow cytometry as described above. The DiOC6 dye is a reagent for measuring mitochondrial activity and is a reagent that can perform measurement based on the attenuation of the amount of fluorescence by cytotoxicity (cell death, etc.). Cytotoxicity (cell death, etc.) was confirmed in DMSO-supplemented HUVECs cultured under heat stress load as compared to control DMSO-supplemented HUVECs cultured under usual conditions, whereas the addition of auraptene (component A) or tangeretin (component T) at the time of culture under heat stress load increased the number of DiOC6 staining-positive cells thereby to suppress cytotoxicity (e.g., cell death) (FIG. 9).

Figure 10:
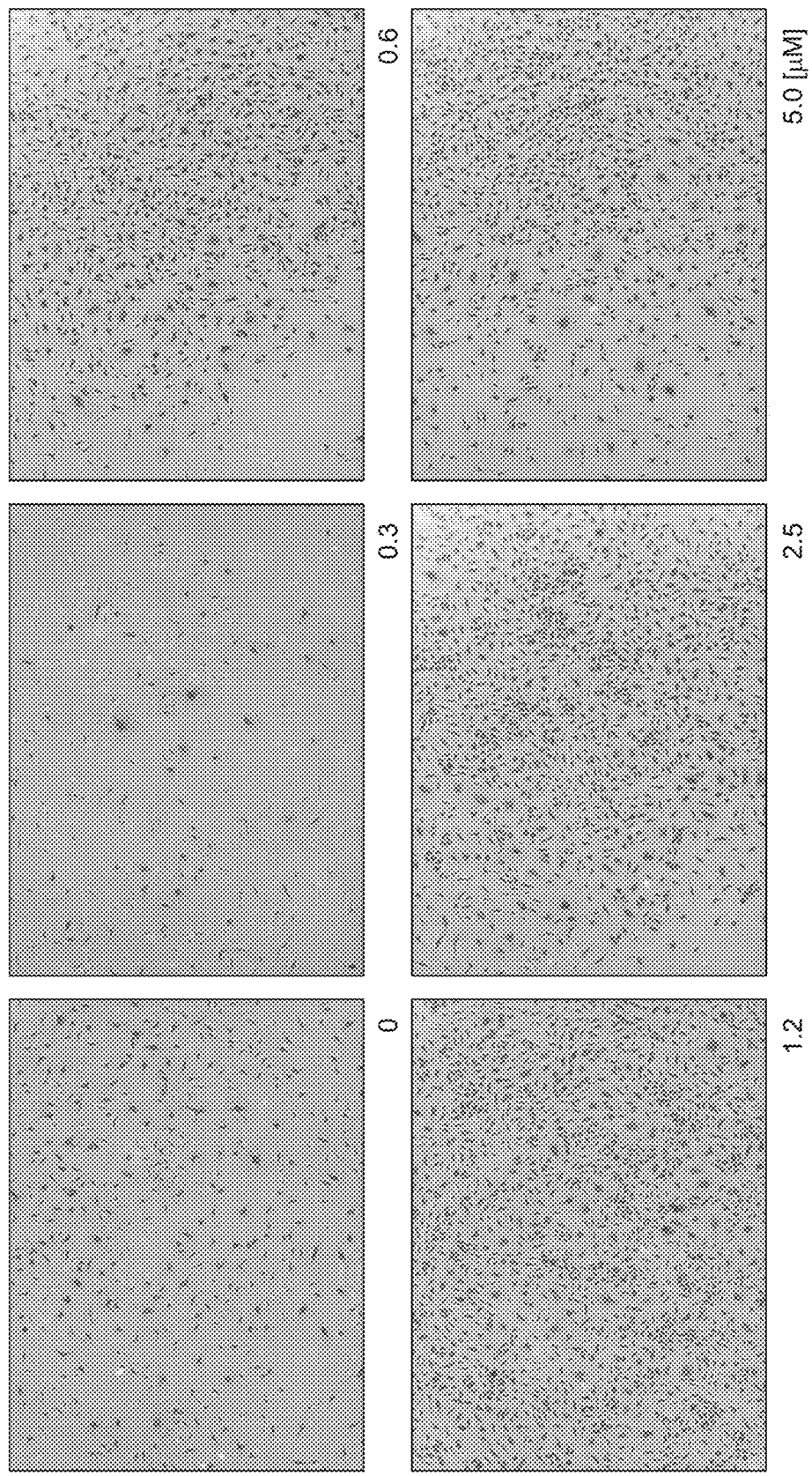
FIG. 10 shows results of a concentration dependency experiment showing the cell death suppressive effect of auraptene. The panels show phase contrast micrographs of cultured cells when human vascular endothelial cells (HUVECs) were cultured at 40° C. for 3 days in a medium containing auraptene at a concentration of 0, 0.3, 0.6, 1.2, 2.5, or 5.0 µM.

As the cell death suppressive effect of auraptene was studied at usual concentrations of 5 to 10 µM, its effective concentration was further studied. Serial dilutions of auraptene were added to the cells, and the cell death of the HUVECs caused by heat stress was observed by crystal violet staining. As a result, the suppressive effect was able to be confirmed up to the concentration of 0.6 µM (600 mM) (FIG. 10).

Figure 11:
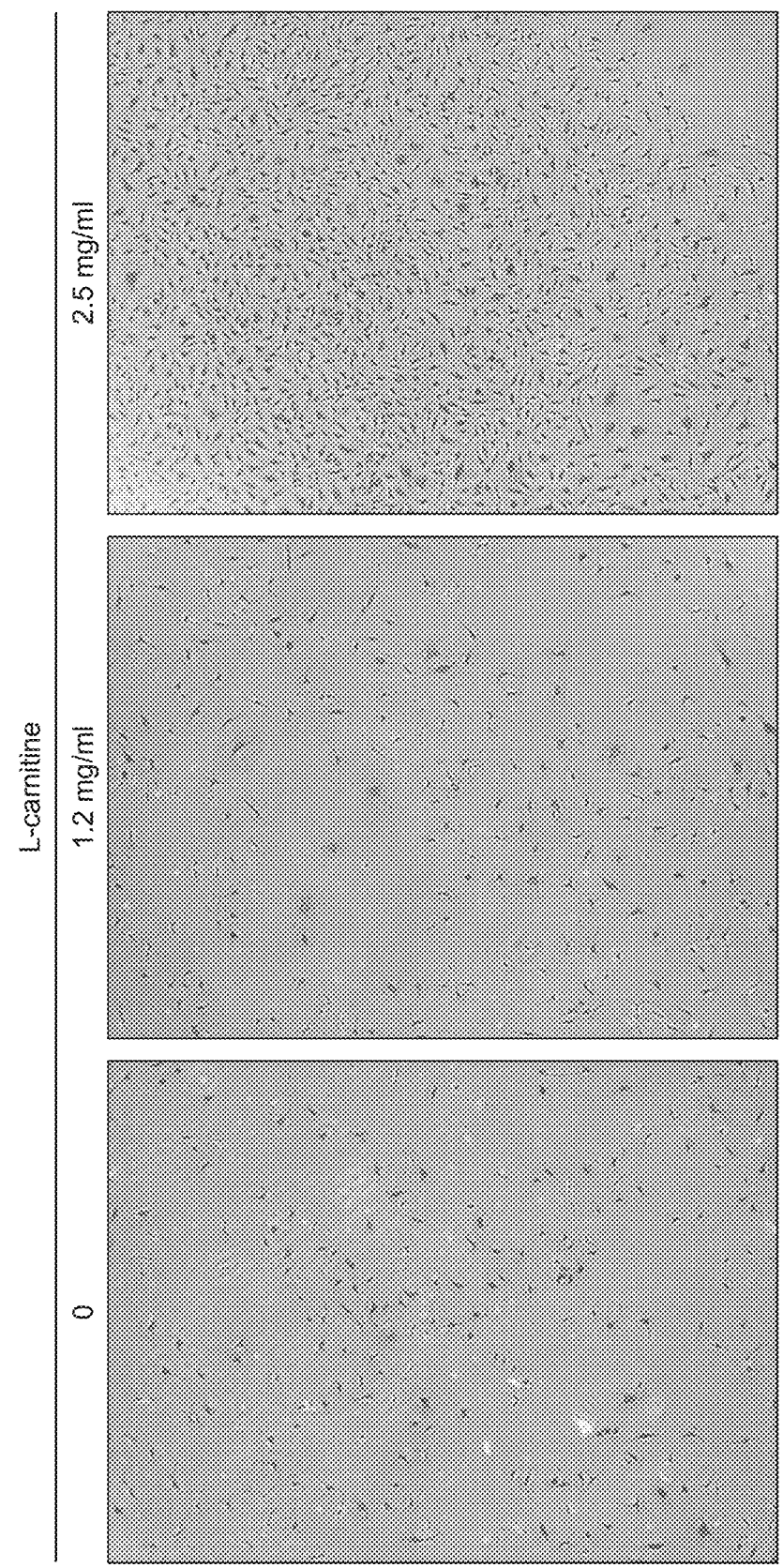
FIG. 11 shows results of a concentration dependency experiment showing the cell death suppressive effect of L-carnitine, which was conducted for comparison to the results about auraptene (FIG. 10). The panels show phase contrast micrographs of cultured cells when human vascular endothelial cells (HUVECs) were cultured at 40° C. for 3 days in a medium containing L-carnitine at a concentration of 0, 1.2, or 2.5 mg/ml.

By contrast, the suppressive effect was observed at 2.5 mg/ml (15 mM) when L-carnitine reportedly effective for fatty acid metabolism was added (FIG. 11). In short, L-carnitine requires approximately 25000 times the concentration of auraptene, demonstrating that the effect of auraptene is markedly strong.

(6) Analysis on Intracellular Localization of Fat Droplets

A supernatant of human vascular endothelial cells (HUVECs) cultured in a 10-cm dish was removed with an aspirator. Then, 2 mL of trypsin/EDTA was added to the cells, and the cells were detached by incubation at 37° C. in a 5% $CO_2$ environment. After the cell detachment, 5 mL/dish of a culture medium was added, and the cells were transferred to a 15-mL tube and centrifuged at 1200 rpm for 5 minutes in a centrifuge. The supernatant was removed, and then, the number of cells was adjusted to a cell density of $5\times10^4$ cells/mL using a cell counting kit by the addition of 5 mL of a culture medium. Then, nine 35-mm dishes were provided, and 2 mL/dish of the solution with the adjusted HUVEC density was inoculated. Auraptene (10 mM) and tangeretin (10 mM) were each added at 2 µL (final concentration: 10 µM)/dish to three dishes. Also, DMSO was added at 2 µL/dish to the remaining 3 dishes to prepare a control. The cells were incubated at 37° C. for 1 day in the presence of 5% $CO_2$, and 1 day later, two of the dishes of each group were incubated at 40° C. for 2 to 3 days in 5% $CO_2$ while the other dishes were incubated at 37° C. for 3 days in 5% $CO_2$.

The supernatant of the HUVECs cultured in each 35-mm dish was removed, and 2 mL/dish of 4% paraformaldehyde in a phosphate buffer solution was added. The cells were left standing at room temperature for 1 hour for cell fixation. The solution was removed, and then, the cells were rinsed twice. 1 mL/dish of BODIPY diluted 2000-fold with a FACS buffer was added, and the cells were left standing at room temperature for 30 minutes in the dark for reaction.

The solution was removed, and then, the cells were rinsed twice. Two drops of Diamond Antifade Mountant with DAPI were added to the cells, and a round glass cover was put on the cells, followed by fluorescence photographing under a confocal laser scanning microscope.

As a result, no change in the amount of fat droplets was confirmed in the auraptene (AUR)- or tangeretin (TAN)-supplemented HUVECs, as in the control DMSO-supplemented HUVECs, at the time of usual culture, whereas decrease in the amount of fat droplets was confirmed in the auraptene- or tangeretin-supplemented HUVECs cultured under heat stress load for 2 days (FIGS. 12A, 12B and 12C). This suggested that these components enhanced intracellular fatty acid metabolism.

(7) Analysis on Localization of ABCD3, PPARα and PPARγ

A supernatant of human vascular endothelial cells (HUVECs) cultured in a 10 cm dish was removed with an aspirator. Then, 2 mL of trypsin/EDTA was added to the cells, and the cells were detached by incubation at 37° C. in a 5% $CO_2$ environment. After the cell detachment, 5 mL/dish of a culture medium was added, and the cells were transferred to a 15-mL tube and centrifuged at 1200 rpm for 5 minutes in a centrifuge. The supernatant was removed, and then, the number of cells was adjusted to a cell density of $5\times10^4$ cells/mL using a cell counting kit by the addition of 5 mL of a culture medium. Then, six 35-mm dishes were provided, and 2 mL/dish of the solution with the adjusted HUVEC density was inoculated. Auraptene (10 mM) and tangeretin (10 mM) were each added at 2 µL (final concentration: 10 µM)/dish to two dishes. Also, DMSO was added at 2 µL/dish to the remaining 2 dishes to prepare a control. The cells were incubated at 37° C. for 1 day in 5% $CO_2$, and 1 day later, the dishes of each group were incubated at 37° C. and 40° C., respectively, for 2 days in 5% $CO_2$.

The supernatant of the HUVECs cultured in each 35-mm dish was removed, and 2 mL/dish of 4% paraformaldehyde in a phosphate buffer solution was added. The cells were left standing at room temperature for 1 hour.

The solution was removed, and then, the cells were rinsed twice. 2 mL/dish of 0.5% Triton-X00 (Wako Pure Chemical Industries, Ltd.) in PBS was added, and the cells were left standing at room temperature for 5 minutes. The solution was removed, and then, the cells were rinsed twice. 1 mL/dish of an anti-ABCD3 antibody, an anti-PPARα antibody or an anti-PPARγ antibody, each of which was diluted 150-fold with a FACS buffer, was added, and the cells were left standing at room temperature for 2 hours for reaction.

The solution was removed, and then, the cells were rinsed twice. 1 mL/dish of DyLight 649-labeled anti-Rabbit IgG antibody diluted 500-fold with a FACS buffer was added, and the cells were left standing at room temperature for 1 hour in the dark for reaction. The solution was removed, and then, the cells were rinsed twice. Two drops of Diamond Antifade Mountant with DAPI were added to the cells, and a round glass cover was put on the cells, followed by fluorescence photographing under a confocal laser scanning microscope.

As a result, as for change in the expression of PPARα, no change in the expression level of PPARα was observed in the human vascular endothelial cells (HUVECs) placed under heat stress load, as in the control DMSO (dimethyl sulfoxide)-supplemented HUVECs, both for usual culture and for culture under heat stress load, whereas increase in the expression of PPARα was observed in the auraptene (AUR)- or tangeretin (TAN)-supplemented HUVECs cultured under culture conditions of 40° C. and 1 day (FIGS. 13A, 13B and 13C). This result was consistent with evidently increased expression in real-time PCR and Western blotting.

As for change in the expression of PPARγ, no change in the expression level of PPARγ was observed in the human vascular endothelial cells (HUVECs) placed under heat stress load, as in the control DMSO-supplemented HUVECs, both for usual culture and for culture under heat stress load, whereas increase in the expression of PPARγ was observed in the auraptene (AUR)-supplemented vascular endothelial cells cultured under culture conditions of 40° C. and 1 day (FIGS. 14A, 14B and 14C). The increasing effect was not observed in the addition of tangeretin (TAN). These effects were also confirmed by real-time PCR As for change in the expression of ABCD3, change in the expression of ABCD3 was not observed in both the control DMSO-supplemented and auraptene (AUR)- or tangeretin (not shown)-supplemented human vascular endothelial cells (HUVECs) placed under heat stress load, both for usual culture and for culture under heat stress load (FIGS. 15A and 15B).

(8) Effect of Suppressing Inflammatory Cytokines in Lymphocytes Under Heat Stress Load by Addition of Auraptene <IL-6 Concentration Measurement>

10 mL of human peripheral blood was collected and anti-coagulated with heparin, and 10 mL of PBS(−) was added thereto and stirred. 15 mL of Lymphocyte Separation Medium 1077 (PromoCell GmbH) was layered thereon so as not to mix blood thereinto, followed by blood separation at 1600 rpm for 30 minutes in a centrifuge. The mononuclear cell layer thus separated was collected into a dropper, added to 20 mL of a culture medium, and centrifuged at 1500 rpm for 5 minutes in a centrifuge. The supernatant was removed, and then, 20 mL of a culture medium was added to the cells and stirred. The cells were centrifuged again at 1500 rpm for 5 minutes in a centrifuge. The supernatant was removed, and then, 10 mL of a culture medium was added to the cells and stirred. The whole amount was added to a 10-cm dish and incubated at 37° C. for 1 hour in a 5% $CO_2$ environment. Then, the supernatant (lymphocytes) was recovered into a 15-mL tube, and the number of cells was adjusted to a cell density of $1\times10^5$ cells/mL using a cell counting kit. The solution with the adjusted lymphocyte density was inoculated at 4 mL/well to 2 wells of each 6-well plate. Auraptene (10 mM) was added at 4 µL (final concentration: 10 µM)/well to one well of each plate. Also, a phytochemical dissolving solution DMSO was added at 4 µL/well to the remaining wells to prepare a control. The cells were incubated at 37° C. for 1 day in the presence of 5% $CO_2$, and 1 day later, incubated at 40° C. for 3 days in 5% $CO_2$. Then, the supernatant was recovered into a 1.5 mL Eppendorf tube and centrifuged at 8000 rpm for 5 minutes in a centrifuge. The supernatant was recovered into a fresh 1.5-mL Eppendorf tube and preserved at −20° C.

Human IL-6 of an ELISA kit was used in IL-6 measurement. 5× Coating Buffer A included in the assay kit was diluted 5-fold with distilled water. Capture Antibody diluted 200-fold with the Coating Buffer was added at 100 µL/well to a 96-well plate, and the plate was left standing overnight at 4° C.

The antibody solution was removed, and each well was washed four times. A very small amount of the reaction solution remaining in the plate was completely removed with Kim Towel. Then, ELISA Assay Diluent (BioLegend, Inc.) diluted 5-fold with distilled water was added at 200 µL/well, and the plate was left standing overnight at 4° C.

The solution was removed, and each well was washed four times. A very small amount of the reaction solution remaining in the plate was completely removed with Kim Towel. IL-6 standard protein was diluted with Assay Diluent to prepare dilution series of the IL-6 standard protein. The dilution series of the IL-6 standard protein and the 40° C. culture supernatant of the lymphocytes were added at 100 µL/well, and the plate was left standing at room temperature for 2 hours. The solution was removed, and each well was washed four times. A very small amount of the reaction solution remaining in the plate was completely removed with Kim Towel. Detection Antibody diluted 200-fold with Assay Diluent was added at 100 µL/well, and the plate was left standing at room temperature for 1 hour. The solution was removed, and each well was washed four times. Avidin-HRP diluted 1000-fold with Assay Diluent was added at 100 µL/well, and the plate was left standing at room temperature for 30 minutes. The solution was removed, and each well was washed five times. A very small amount of the reaction solution remaining in the plate was completely removed with Kim Towel. TMB Microwell Peroxidase Substrate was added at 100 µL/well and reacted for approximately 30 minutes in the dark. The reaction was terminated by the addition of 2 N $H_2SO_4$ at 100 μL/well, followed by the absorbance measurement of the reaction solution in a plate reader at 450 nm.

<CCL-2 Concentration Measurement>

10 mL of human peripheral blood was collected and anti-coagulated with heparin, and 10 mL of PBS(−) was added thereto and stirred. 15 mL of Lymphocyte Separation Medium 1077 (PromoCell GmbH) was layered thereon so as not to mix blood thereinto, followed by blood separation at 1600 rpm for 30 minutes in a centrifuge. The mononuclear cell layer thus separated was collected into a dropper, added to 20 mL of a culture medium, and centrifuged at 1500 rpm for 5 minutes in a centrifuge. The supernatant was removed, and then, 20 mL of a culture solution was added to the cells and stirred. The cells were centrifuged again at 1500 rpm for 5 minutes in a centrifuge. The supernatant was removed, and then, 10 mL of a culture medium was added to the cells and stirred. The whole amount was added to a 10-cm dish and incubated at 37° C. for 1 hour in a 5% $CO_2$ environment. Then, the supernatant (lymphocytes) was recovered into a 15-mL tube, and the number of cells was adjusted to a cell density of $1\times10^5$ cells/mL using a cell counting kit. The solution with the adjusted lymphocyte density was inoculated at 4 mL/well to 2 wells of each 6-well plate. Auraptene (10 mM) was added at 4 μL (final concentration: 10 μM)/well to one well of each plate. Also, a phytochemical dissolving solution DMSO was added at 4 μL/well to the remaining wells to prepare a control. The cells were incubated at 37° C. for 1 day in 5% $CO_2$, and 1 day later, incubated at 40° C. for 3 days in the presence of 5% $CO_2$. Then, the supernatant was recovered into a 1.5-mL Eppendorf tube and centrifuged at 8000 rpm for 5 minutes in a centrifuge. The supernatant was recovered into a fresh 1.5-mL Eppendorf tube and preserved at −20° C.

Human MCP1/CCL2 of an ELISA kit was used in CCL-2 measurement.

5× Coating Buffer included in the assay kit was diluted 5-fold with distilled water. Capture Antibody diluted 200-fold with the Coating Buffer was added at 100 μL/well to a 96-well plate, and the plate was left standing overnight at 4° C.

The antibody solution was removed, and each well was washed four times. A very small amount of the reaction solution remaining in the plate was completely removed with Kim Towel. Then, ELISA Assay Diluent (BioLegend, Inc.) diluted 5-fold with distilled water was added at 200 μL/well, and the plate was left standing overnight at 4° C.

The solution was removed, and each well was washed four times. A very small amount of the reaction solution remaining in the plate was completely removed with Kim Towel. MCP1/CCL2 standard protein was diluted with Assay Diluent to prepare dilution series of the MCP1/CCL2 standard protein. The dilution series of the MCP1/CCL2 standard protein and the 40° C. culture supernatant of the lymphocytes were added at 100 μL/well, and the plate was left standing at room temperature for 2 hours. The solution was removed, and each well was washed four times. A very small amount of the reaction solution remaining in the plate was completely removed with Kim Towel. Detection Antibody diluted 200-fold with Assay Diluent was added at 100 μL/well, and the plate was left standing at room temperature for 1 hour. The solution was removed, and each well was washed four times. Avidin-HRP diluted 1000-fold with Assay Diluent was added at 100 μL/well, and the plate was left standing at room temperature for 30 minutes. The solution was removed, and each well was washed five times. A very small amount of the reaction solution remaining in the plate was completely removed with Kim Towel. TMB Microwell Peroxidase Substrate was added at 100 μL/well, followed by the absorbance measurement of the reaction solution in a plate reader at 450 nm.

<Results>

Attention was focused on lymphocytes responsible for body's defense because not only blood vessels but blood undergoes heat stress load when the blood vessels undergo the heat stress load. It was confirmed that the production of inflammatory cytokines (fever promoting factors) IL-6 and CCL-2 was significantly suppressed in the auraptene-supplemented peripheral blood lymphocytes (sample A and sample B) placed under heat stress load (culture at 40° C. for 2 days) as compared to the solvent DMSO-supplemented lymphocytes placed under heat stress load (Table 1, $p<0.05$). Measurement values obtained without the addition of auraptene were used for a control.

TABLE 1

|  | Non-addition [pg/ml] | Addition of auraptene [pg/ml] | P value |
|---|---|---|---|
| IL-6 sample A | 10 ± 1.1 | 5 ± 0.3 | 0.0018 |
| IL-6 sample B | 18 ± 0.8 | 10 ± 0.1 | 0.0119 |
| CCL-2 sample A | 61 ± 0.2 | 32 ± 1.7 | 0.0116 |

The test results of the sections (1) to (8) will be summarized below.

Results of measuring change (increase or decrease) in cytotoxicity (cell death), the amount of fat droplets accumulated, the amount of PPARγ, the amount of PPARα, and the amount of pyrogenic factors (inflammatory cytokines; e.g., IL-6 and CCL-2) when human vascular endothelial cells (HUVECs) were cultured at 40° C. in a medium alone, a tangeretin-containing medium, or an auraptene-containing medium are summarized in Table 2. In this context, measurement results about human vascular endothelial cells (HUVECs) cultured at 37° C. were used as a comparative control.

TABLE 2

|  | 40° C. | Addition of tangeretin 40° C. | Addition of auraptene 40° C. |
|---|---|---|---|
| Cytotoxicity (cell death) | Increased | Suppressed | Suppressed |
| Amount of fat droplets | Unchanged | Decreased | Decreased |
| PPARγ | Decreased | Increased | Unchanged |
| PPARα | Decreased | Increased | Increased |
| Pyrogenic factor | Increased | — | Decreased |

As seen from Table 2, auraptene and tangeretin suppressed the cytotoxicity (cell death, etc.) of vascular endothelial cells caused by the load of heat stress, increased lipid metabolism, and further decreased the production and release of pyrogenic factors in lymphocytes which are blood cells. Therefore, these components suppressed or alleviated the cytotoxicity of the vascular endothelial cells due to heat stress, demonstrating that the components are effective for preventing, alleviating or treating a heat illness.

Example 2

<Suppression of Cytotoxicity of Vascular Endothelial Cells Under Heat Stress Load by Medium Chain Fatty Acid>

1. Material (1) Human Normal Cell Line

Human umbilical vein vascular endothelial cells (HUVECs: purchased from Kurabo Industries Ltd. (Japan)) were used in this Example.

(2) Cell Culture Medium

To HuMedia-EB2 (Kurabo Industries Ltd.), 2% fetal bovine serum (FBS), hEGF, hydrocortisone, an antimicrobial agent, hFGF-B, and heparin were added, and the resulting medium was used as a HUVEC culture medium.

2. Experiment (1) Experiment on Suppression of Cell Death by Addition of Medium Chain Fatty Acid HUVECs were seeded at a cell density of $5\times10^4$ cells/well to a 6-well plate. Varying concentrations of medium chain fatty acid were added to the cells, and the cells were cultured at 37° C. for 1 day. The medium chain fatty acid MCT oil (The Nisshin OilliO Group, Ltd. (Japan)) was bound to defatted bovine serum albumin (BSA) and added with its concentration adjusted to the culture solution (8 µl/ml and 64 µl/ml). The concentrations of the medium chain fatty acid were set to 64 µL/ml as the highest concentration, which was decreased by half to concentrations of 32 µL, 16 µL, 8 µL, and 4 µL (lowest concentration). Also, cells were provided without the addition of the medium chain fatty acid for a control. The cells were cultured for 1 day from the addition of the medium chain fatty acid, exposed to heat stress of 40° C. for approximately 3 days, and used in measurement.

(2) Cell Fixation and Staining

The culture solution of the vascular endothelial cells thus cultured was removed, and a 4% paraformaldehyde solution was added at 1 mL/well. The cells were left standing at room temperature for 30 minutes for cell fixation. The 4% paraformaldehyde solution was removed, and each well was washed twice with 1×PBS. A crystal violet staining solution was added at 1 mL/well, and the cells were left overnight. The staining solution was removed, and 1×PBS was added at 1 mL/well, followed by the observation and photographing of the cells under a phase contrast microscope.

(3) Detection of Apoptosis (Cell Death)

ApoScreen Annexin V (Cosmo Bio Co., Ltd.) was used for quantifying the rate of dead cells. The culture solution in the 6-well plate is recovered into a 15-mL tube. 1×PBS was added at 1 mL/well to the plate and left for 2 minutes, and the 1×PBS was recovered into the 15-mL tube. The cells were detached by the addition of trypsin at 1 mL/well. RPMI medium was added at 2 mL/well and recovered into the 15-mL tube, which was then applied to a centrifuge at 1200 rpm for 5 minutes. The supernatant was removed, and the tube was washed twice to prepare pellets. The pellets were recovered by the addition of 100 µL of Annexin Binding Buffer to the 15-ml tube, and transferred to a FACS tube. 10 µL of Annexin V was added thereto, and the tube was left standing at 4° C. for 15 minutes. To the tube, 380 µL of Annexin Binding Buffer was added, and 10 µL of 7-AAD was added, followed by measurement by flow cytometry.

(4) ELISA Kit

The concentration of HSP70 produced from the vascular endothelial cells placed under heat stress load was measured using Human HSP70/HSP1A (R&D Systems, Inc.). The measurement method was performed in accordance with the manufacturer's protocol.

3. Results

Figure 16:
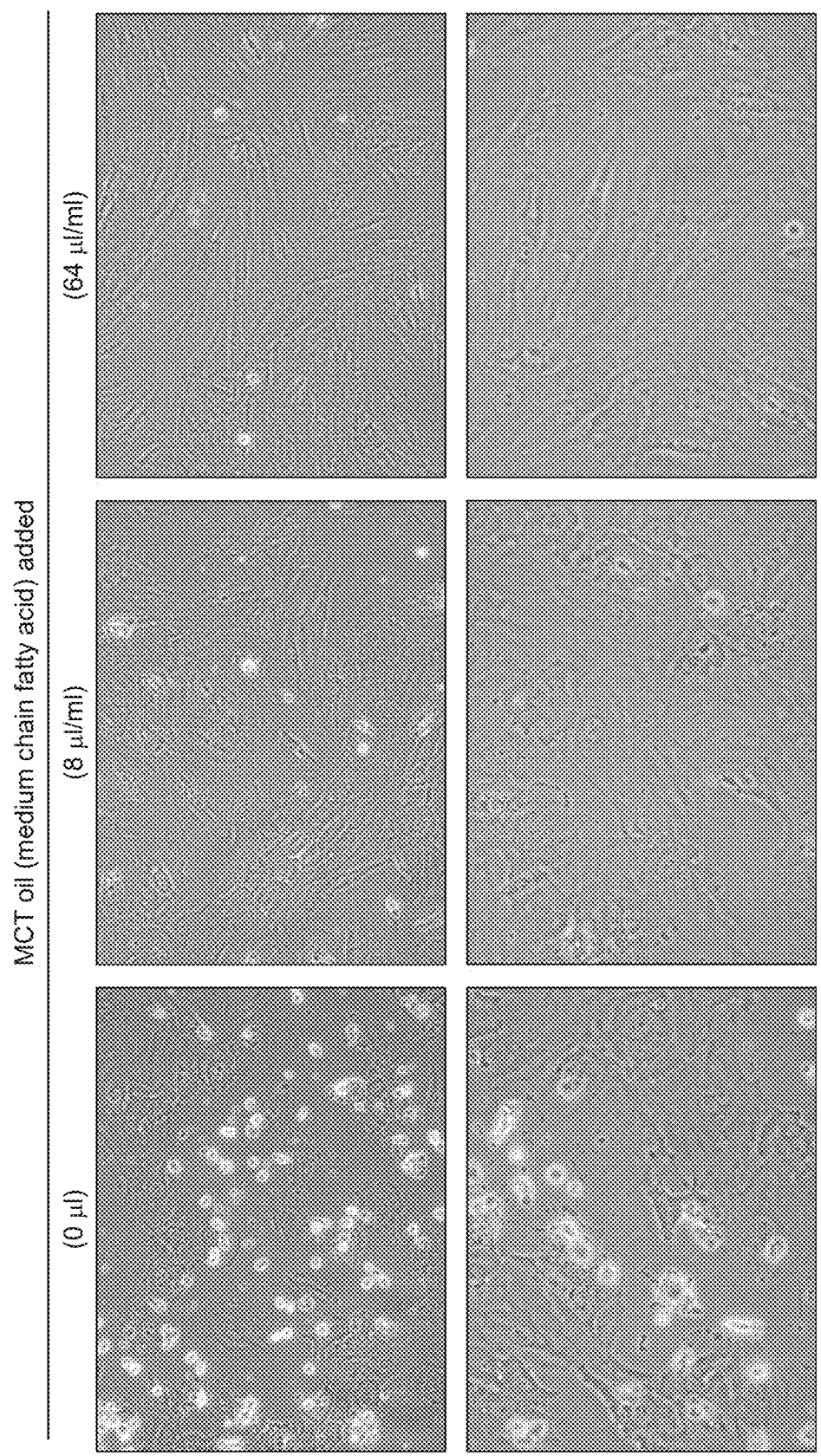
FIG. 16 shows the heat stress resistant effect of medium chain fatty acid (0 µl/ml, 8 µl/ml, and 64 µl/ml) when human vascular endothelial cells (HUVECs) were cultured at 40° C. for 3 days. The upper panels and the lower panels show phase contrast micrographs taken at magnifications of ×100 and ×200, respectively. In the figure, the medium chain fatty acid used was MCT (medium chain triglyceride) oil (The Nisshin OilliO Group, Ltd., Japan) which is composed mainly of C8 to C12 medium chain fatty acid.
Figure 17:
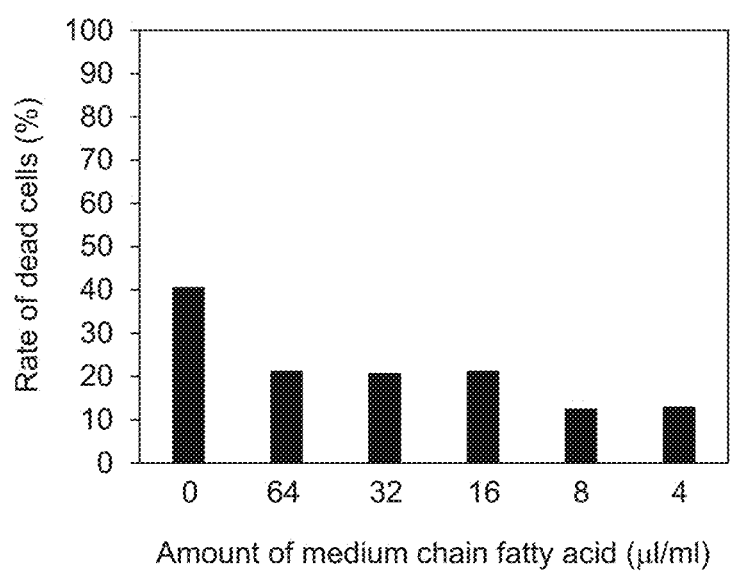
FIG. 17 shows the relationship between the rate of dead cells (%) and the amount of medium chain fatty acid (µl/ml) of human vascular endothelial cells (HUVECs) caused by the load of heat stress. In the figure, the medium chain fatty acid used was MCT (medium chain triglyceride) oil (The Nisshin OilliO Group, Ltd., Japan) which is composed mainly of C8 to C12 medium chain fatty acid.

As a result of culturing vascular endothelial cells by the addition of medium chain fatty acid, and on the next day, culturing the cells under heat stress of 40° C., suppression of cell death, i.e., increase in the number of live cells, was found (FIG. 16). As a result of quantifying the ratio of dead cells by annexin staining, 40% dead cells were observed under culture conditions involving no addition of the medium chain fatty acid, whereas a cell death suppressive effect (approximately 50%) was found at each concentration from 4 to 64 µl/ml of the added medium chain fatty acid (FIG. 17).

Figure 18:
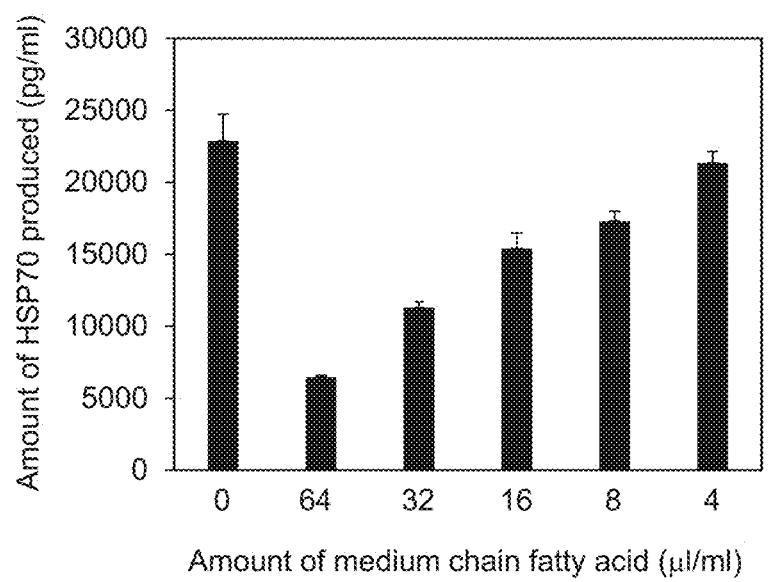
FIG. 18 shows the relationship between the amount of medium chain fatty acid (µl/ml) and the amount of HSP70 produced (pg/ml) when human vascular endothelial cells (HUVECs) underwent the load of heat stress. In the figure, the medium chain fatty acid used was MCT (medium chain triglyceride) oil (The Nisshin OilliO Group, Ltd., Japan) which is composed mainly of C8 to C12 medium chain fatty acid.

The addition of the medium chain fatty acid was found to decrease the amount of HSP70 produced from the cells in a concentration-dependent manner (FIG. 18).

The addition of auraptene was found to increase the overall number of cells at 37° C. (FIG. 19A, left), and further, the addition of the medium chain fatty acid increased the number of live cells thereof (FIGS. 19B and 19C, middle and right). This indicates that the medium chain fatty acid can further enhance the effect of suppressing heat stress by auraptene.

INDUSTRIAL APPLICABILITY

The present invention is industrially useful because, through the use of the cytotoxicity of cells such as vascular endothelial cells due to heat stress, at least one substance selected from the group consisting of phytochemicals auraptene (one kind of coumarin) and tangeretin (one kind of polymethoxyflavonoid) and medium chain fatty acid has been found to be effective for protecting cells such as vascular endothelial cells from heat stress, and preventing, alleviating and/or treating a heat illness.

All publications, patents and patent applications cited herein are incorporated herein by reference in their entirety.

The invention claimed is:

1. A composition for preventing, alleviating and/or treating a heat illness in a subject, comprising:
   at least one active ingredient selected from the group consisting of auraptene and tangeretin, wherein the amount of active ingredient(s) in the composition is 0.04 mg or larger; and
   an emulsifying agent;
   wherein the composition is in a form of an emulsion.

2. The composition according to claim 1, wherein the heat illness comprises the cytotoxicity of vascular endothelial cells caused by load of heat stress.

3. The composition according to claim 1 or 2, wherein the heat illness comprises aberration associated with the production and release of a fever-inducing inflammatory cytokine(s) from blood cells caused by load of heat stress.

4. The composition according to claim 1, wherein the composition has at least one effect selected from the group consisting of:
   an effect of suppressing the cytotoxicity of vascular endothelial cells caused by load of heat stress,
   an effect of increasing lipid metabolism, and
   an effect of decreasing the production and release of a fever-inducing inflammatory cytokine(s) from blood cells caused by load of heat stress.

5. The composition according to claim 1, wherein the subject is a homeothermic animal.

6. The composition according to claim 5, wherein the homeothermic animal is a human, a livestock animal, or a pet animal.

7. The composition according to claim 1, wherein auraptene and/or tangeretin is a synthetic substance, or is from an extract of a plant material of a citrus.

8. The composition according to claim 7, wherein the plant material is a fruit.

9. The composition according to claim 7, wherein auraptene is from a fruit extract of at least one citrus selected from the group consisting of *Citrus natsudaidai, Citrus hassaku, Citrus* x *paradisi, Citrus junos, Citrus sphaerocarpa,* and *Citrus grandis*.

10. The composition according to claim 7, wherein tangeretin is from a fruit extract of at least one citrus selected from the group consisting of *Citrus reticulata* and *Citrus depressa*.

11. The composition according to claim 1, wherein the composition is a food, a drink, or a medicament.

12. The composition according to claim 1, wherein the composition is an animal feed or a feed additive.

13. The composition according to claim 1, wherein the at least one of auraptene and/or tangeretin is extracted with a solvent selected from the group consisting of water, ethanol, methanol, isopropanol, propylene glycol, diethyl ether, hexane, acetone, acetonitrile, ethyl acetate, or a mixture of two or more of the solvents.

14. The composition according to claim 1, wherein the at least one of auraptene and/or tangeretin is from an extract of a plant material of a citrus, wherein the extract comprises extracts, squeezes, and mixtures thereof, and concentrates or dry products obtained by concentrating or drying the squeezes, the extracts, or the mixtures thereof.

15. The composition of claim 1, further comprising one or more non-active ingredient selected from the group consisting of an excipient, an extender, a disintegrant, a lubricant, a binder, an antioxidant, a colorant, an anti-aggregation agent, an absorption promoter, a solvent, a solubilizer, a tonicity agent, a stabilizer, a corrigent, an antiseptic, a pH adjuster, wherein the non-active ingredient is acceptable as a pharmaceutical or a food or drink or acceptable as animal feed or a feed additive.

16. A composition for preventing, alleviating and/or treating a heat illness in a subject, comprising:
 auraptene and tangeretin as the active ingredients, wherein auraptene and tangeretin are from extracts of a plant material of a citrus, wherein the amount of auraptene and tangeretin in the composition is 0.04 mg or larger; and
 an emulsifying agent;
 wherein the composition is in a form of an emulsion.

17. The composition according to claim 16, wherein auraptene is from a fruit extract of at least one citrus selected from the group consisting of *Citrus natsudaidai, Citrus hassaku, Citrus* x *paradisi, Citrus junos, Citrus sphaerocarpa,* and *Citrus grandis*.

18. The composition according to claim 16, wherein tangeretin is from a fruit extract of at least one citrus selected from the group consisting of *Citrus reticulata* and *Citrus depressa*.

19. The composition of claim 16, further comprising one or more non-active ingredient selected from the group consisting of an excipient, an extender, a disintegrant, a lubricant, a binder, an antioxidant, a colorant, an anti-aggregation agent, an absorption promoter, a solvent, a solubilizer, a tonicity agent, a stabilizer, a corrigent, an antiseptic, a pH adjuster, wherein the non-active ingredient is acceptable as a pharmaceutical or a food or drink or acceptable as animal feed or a feed additive.

20. A method for preventing, alleviating and/or treating a heat illness, or cytotoxicity of vascular endothelial cells caused by load of heat stress and/or aberration associated with the production and release of a fever-inducing inflammatory cytokine(s) from blood cells caused by load of heat stress in a subject, comprising administering or providing a composition according to claim 1 to the subject.

* * * * *